US012406750B2

(12) United States Patent
Feitosa et al.

(10) Patent No.: US 12,406,750 B2
(45) Date of Patent: Sep. 2, 2025

(54) ENCODING DIGITAL DATA USING OLIGONUCLEOTIDES

(71) Applicant: Lenovo (Singapore) Pte. Ltd., Singapore (SG)

(72) Inventors: Allan Eduardo Feitosa, Butantã (BR); Thiago Yuji Aoyagi, Butantã (BR); Adriano Galindo Leal, Butantã (BR); Andre Guilherme da Costa-Martins, Butantã (BR); Cristina Maria Ferreira da Silva, Butantã (BR); Diego Trindade de Souza, Butantã (BR); Eduardo Takeo Ueda, Butantã (BR); Marcelo Gonzaga de Oliveira Parada, Butantã (BR); Bruno Marinaro Verona, Butantã (BR)

(73) Assignee: Lenovo (Singapore) Pte. Ltd., Singapore (SG)

(*) Notice: Subject to any disclaimer, the term of this patent is extended or adjusted under 35 U.S.C. 154(b) by 113 days.

(21) Appl. No.: 18/459,312

(22) Filed: Aug. 31, 2023

(65) Prior Publication Data
US 2025/0078958 A1 Mar. 6, 2025

(51) Int. Cl.
G16B 50/50 (2019.01)
G16B 30/10 (2019.01)
G06N 3/12 (2023.01)

(52) U.S. Cl.
CPC .......... *G16B 50/50* (2019.02); *G16B 30/10* (2019.02); *G06N 3/12* (2013.01)

(58) Field of Classification Search
CPC .......... G16B 50/50; G16B 30/10; G06N 3/12; G06N 3/23; G06F 19/00
See application file for complete search history.

(56) References Cited

U.S. PATENT DOCUMENTS 9,384,320 B2 * 7/2016 Church .................. G06N 3/123

OTHER PUBLICATIONS

Blawat, Meinolf, "Forward error correction for DNA data storage", Procedia Computer Science, vol. 80, 2016, pp. 1011-1022, (2016), 12 pgs.

Bornholt, James, "A DNA based archival storage system", ACM SIGOPS Operating Systems Review, vol. 50, No. 2, pp. 637-649, 2016, (2016), 13 pgs.

Cao, "Minimum free energy coding for DNA storage", IEEE Transactions on Nanobioscience, vol. 20, No. 2, pp. 212-222, 2021., (2020), 11 pgs.

(Continued)

*Primary Examiner* — Joseph J Lauture
(74) *Attorney, Agent, or Firm* — Schwegman Lundberg & Woessner, P.A.

(57) ABSTRACT

Various aspects disclosed relate to encoding digital data as oligonucleotides and retrieving the digital data from the oligonucleotides via one or more decoding processes. Digital data can be encoded using oligonucleotides by determining a string of characters that corresponds to the digital data according to an encoding scheme such that individual characters of the string of characters are represented by a nucleotide included in at least one of deoxyribonucleic acid (DNA) or ribonucleic acid (RNA). The string of characters can undergo one or more additional encoding processes to generate additional nucleic acid representations that correspond to the digital data.

20 Claims, 9 Drawing Sheets

Specification includes a Sequence Listing.

(56) References Cited

OTHER PUBLICATIONS

Church, George M., "Next-generation digital information storage in DNA", Science, vol. 337, No. 6102, pp. 1628, 2012., (2012), 2 pgs.
Erlich, Yaniv, "Fountain enables a robust and efficient storage architecture", Science, vol. 355, No. 6328, pp. 950-954, 2017., (2017), 5 pgs.
Fei, Peng, "Ldpc Codes for Portable DNA Storage", IEEE International Symposium on Information Theory, pp. 76-80, 2019., (2019), 6 pgs.
Goldman, Nick, "Towards practical, high-capacity, low-maintenance information storage in synthesized DNA", Nature, vol. 494, No. 7435, pp. 77-80, 2013., (Feb. 7, 2013), 9 pgs.
Grass, Robert N., "Robust chemical preservation of digital information on DNA in silica with error-correcting codes", Angewandte Chemie International Edition, vol. 54, No. 8, pp. 2552-2555, 2015., (2015), 4 pgs.
Organick, Lee, "Random access in large-scale DNA data storage", Nature Biotechnology, vol. 36, pp. 242-248, 2018., (2018), 9 pgs.
Ping, Zhi, "Towards practical and robust DNA-based data archiving using the yin-yang codec system", Nature Computational Science, vol. 2, pp. 234-242, 2022., (2022), 11 pgs.
Reuter, Jason, "High-Throughput Sequencing Technologies", Molecular Cell 58, May 21, 2015, (May 21, 2015), 12 pgs.
Wang, Yixin, "Construction of bio-constrained code for DNA data storage", IEEE Communication Letters, vol. 23, No. 6, pp. 963-966, 2019, (2019), 5 pgs.

\* cited by examiner

SEQUENCE LISTING

```
Sequence total quantity: 7
SEQ ID NO: 1              moltype = DNA   length = 30
FEATURE                   Location/Qualifiers
misc_feature              1..30
                          note = Example Oligonucleotide
source                    1..30
                          mol_type = other DNA
                          organism = synthetic construct
SEQUENCE: 1
accccacacc gcgcgcgcgc tttactttcc                                    30

SEQ ID NO: 2              moltype = DNA   length = 10
FEATURE                   Location/Qualifiers
misc_feature              1..10
                          note = Example Oligonucleotide
source                    1..10
                          mol_type = other DNA
                          organism = synthetic construct
SEQUENCE: 2
tgactgacca                                                          10

SEQ ID NO: 3              moltype = DNA   length = 10
FEATURE                   Location/Qualifiers
misc_feature              1..10
                          note = Example Oligonucleotide
source                    1..10
                          mol_type = other DNA
                          organism = synthetic construct
SEQUENCE: 3
acgatggaca                                                          10

SEQ ID NO: 4              moltype = DNA   length = 10
FEATURE                   Location/Qualifiers
misc_feature              1..10
                          note = Example Oligonucleotide
source                    1..10
                          mol_type = other DNA
                          organism = synthetic construct
SEQUENCE: 4
gactggctag                                                          10

SEQ ID NO: 5              moltype =    length =
SEQUENCE: 5
000

SEQ ID NO: 6              moltype = DNA   length = 23
FEATURE                   Location/Qualifiers
misc_feature              1..23
                          note = Example Oligonucleotide
source                    1..23
                          mol_type = other DNA
                          organism = synthetic construct
SEQUENCE: 6
gctatactta ggaaagcgcg cat                                           23

SEQ ID NO: 7              moltype =    length =
SEQUENCE: 7
000
```

ENCODING DIGITAL DATA USING OLIGONUCLEOTIDES

SEQUENCE LISTING

This application contains a Sequence Listing which has been submitted electronically in ST26 format and is hereby incorporated by reference in its entirety. Said ST26 file, created on Aug. 21, 2023, is named "RSP920230006-US-NP (2707115US1).xml" and is 7,605 bytes in size.

BACKGROUND

Digital data is often recorded on media that allow the digital data to be retrieved using a computing device. The media can include computer memory that stores information using semiconductor technologies. For example, digital data can be stored by memory cells that include transistors, capacitors, impedance devices, and other electronic components made from semiconductor materials. Computer memory can include non-volatile memory devices, such as flash memory and various types of read-only memory. Computer memory can also include volatile memory devices, such as a number of types of random access memory.

SUMMARY OF THE DISCLOSURE

One or more aspects disclosed herein relate to encoding digital data using oligonucleotides. In one or more examples, processes to encode digital data using oligonucleotides can include obtaining an amount of digital data and determining a string of characters that corresponds to the digital data according to an encoding scheme such that individual characters of the string of characters are represented by a nucleotide included in at least one of deoxyribonucleic acid (DNA) or ribonucleic acid (RNA). Additionally, the process can include generating nucleic acid representations based on the string of characters. Individual nucleic acid representations can include a plurality of positions with a portion of the string of characters being distributed among the nucleic acid representations at an individual position across the nucleic acid representations.

In various examples, processes to decode digital data that has been encoded using oligonucleotides can include receiving a request to access at least a portion of the digital data and obtaining a plurality of sequencing reads that correspond to nucleic acid molecules synthesized according to the nucleic acid representations that encoded the digital data. The plurality of sequencing reads can indicate nucleotides present at individual positions of the nucleic acid molecules. In addition, the decoding processes can include performing a process to align individual positions of the plurality of sequencing reads to generate aligned sequencing reads and for a given position of the aligned sequencing reads, determining an additional string of characters that corresponds to nucleotides present at given positions of the aligned sequencing reads. Further, the decoding processes can include generating, using a decoding scheme, a requested portion of the digital data based on the additional string of characters.

In one or more additional examples, processes to encode digital data using oligonucleotides can include obtaining an amount of digital data and determining a string of characters that corresponds to the digital data according to an encoding scheme such that individual characters of the string of characters are represented by a nucleotide included in at least one of deoxyribonucleic acid (DNA) or ribonucleic acid (RNA). Processes to encode digital data using oligonucleotides can also include generating nucleic acid representations based on the string of characters. Individual nucleic acid representations can include a first segment that corresponds to an identifier of the individual nucleic acid representation and a second segment that corresponds to a portion of the digital data. Further, processes to encode digital data using oligonucleotides can include performing, for the individual nucleic acid representations, one or more encryption processes with respect to the second segment of the individual nucleic acid representations based on the first segment of the individual nucleic acid representations to generate a plurality of encoded nucleic acid representations.

BRIEF DESCRIPTION OF THE FIGURES

The drawings illustrate generally, by way of example, but not by way of limitation, various aspects of the present invention.

DETAILED DESCRIPTION OF THE INVENTION

Figure 1:
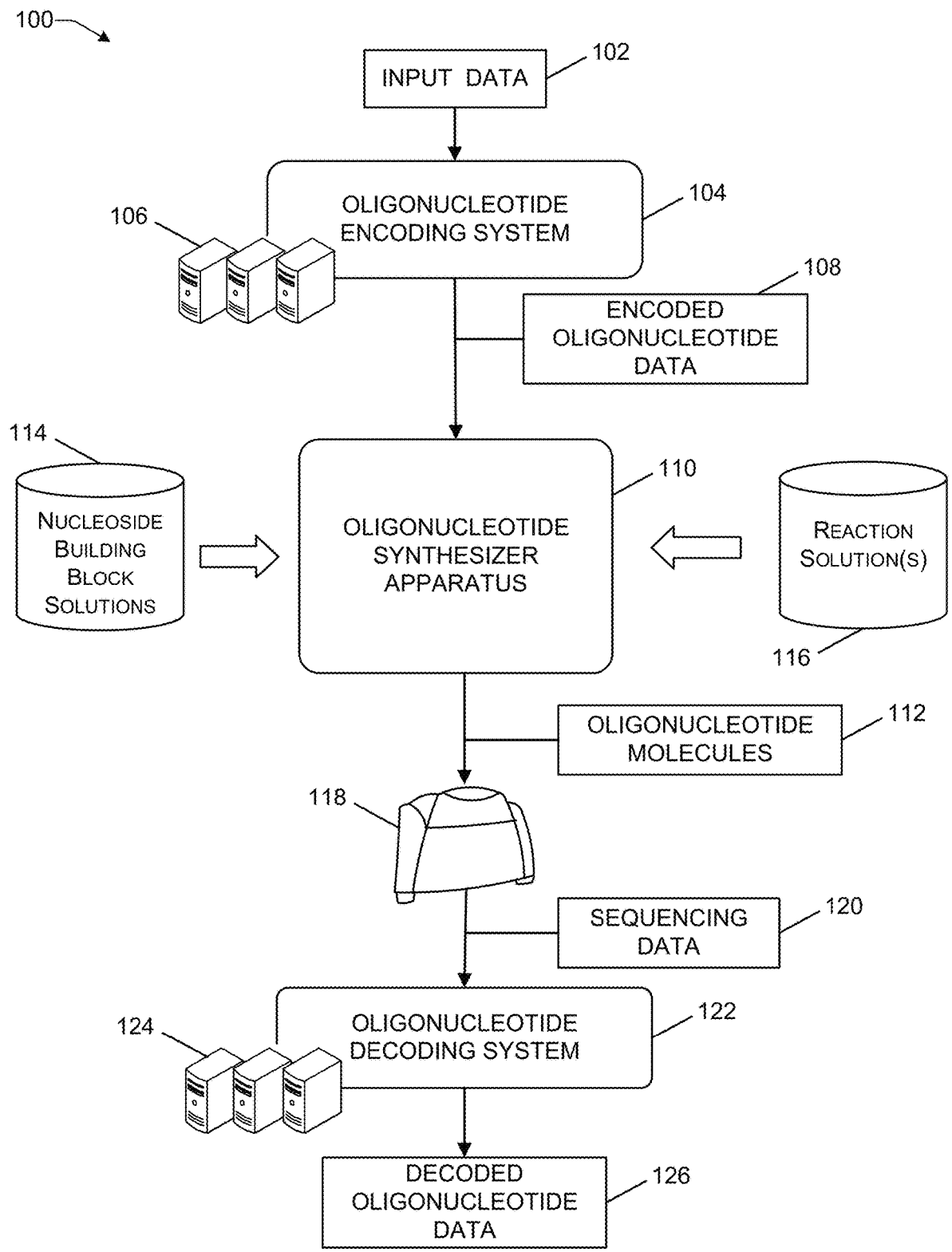
FIG. 1 is diagram of an architecture to encode digital data using oligonucleotides and to decode the digital data stored by the oligonucleotides, in accordance with one or more implementations.

Reference will now be made in detail to certain aspects of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X. Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the inventive subject matter, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The terms "polynucleotide", "nucleic acid", "nucleic acid molecule", "polynucleotide molecule", or "oligonucleotide" refer to a linear polymer of nucleotides or nucleosides joined by internucleosidic linkages. A polynucleotide can comprise at least three nucleotides or three nucleosides. Oligonucleotides often range in size from a few monomeric units, e.g., 3-4, to hundreds of monomeric units. Whenever a polynucleotide is represented by a sequence of letters, such as "ATGCCTG," it will be understood that the nucleotides are in 5'→3' order from left to right and that in the case of DNA, "A" denotes adenosine or deoxyadenosine, "C" denotes cytosine or deoxycytidine, "G" denotes guanine or deoxyguanosine, and "T" denotes thymine or deoxythymidine, unless otherwise noted. The letters A, C, G, and T may be used to refer to the bases themselves, to nucleosides, or to nucleotides comprising the bases, as is standard in the art.

As used herein, "deoxyribonucleic acid" or "DNA" refers to a natural or modified polynucleotide which has a hydrogen group at the 2'-position of the sugar moiety. DNA can include a chain of nucleotides comprising four types of nucleotide bases: adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA can include a chain of nucleotides comprising four types of nucleotides: A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand.

As used herein, "nucleic acid sequencing data", "nucleic acid sequencing information", "sequence information", "nucleic acid sequence", "nucleotide sequence", "sequencing read", or "nucleic acid sequencing read" denotes any information or data that is indicative of the order and identity of the nucleotide bases (e.g., adenine, guanine, cytosine, and thymine or uracil) in a molecule (e.g., oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

The terms, "binary data", "digital information", or "digital data" refers to data encoded using the standard binary code, or a base 2 {0,1} alphabet, data encoded using a hexadecimal base 16 alphabet, data encoded using the base 10 {0-9} alphabet, data encoded using ASCII characters, or data encoded using any other discrete alphabet of symbols or characters in a linear encoding fashion.

In one or more examples, the synthetic production of biopolymers can take place by joining monomer units in at least one of an electrochemical process, a chemical process, or an enzymatic process. In at least some examples, the biopolymers produced using synthetic processes can have fewer nucleotides than biopolymers produced using natural processes within an organism. In one or more illustrative examples, biopolymers produced using synthetic processes can comprise no greater than 1,000 monomer units and biopolymers produced by natural processes within an organism can produce biopolymers having at least thousands, up to tens of thousands, up to millions of monomer units.

In one or more illustrative examples, nucleic acids can be synthesized by adding nucleotides to a molecular scaffold that comprises an intermediate oligonucleotide chain. For example, deoxyribonucleic acid (DNA) molecules and ribonucleic acid (RNA) molecules can be formed by coupling monomer units comprised of adenine (A), guanine (G), cytosine (C), and thymine (T), in the case of DNA, or A, G, C, and uracil (U), in the case of RNA. Typically, synthetic polynucleotides are produced according to a number of predetermined sequences. The predetermined sequences can correspond to at least one of the primers used in polynucleotide sequencing operations. The predetermined sequences can also correspond to identifiers that can be used to identify molecules and/or families of molecules after the sequencing process has been performed. In various examples, the predetermined sequences can correspond to digital data that has been encoded within sequences of oligonucleotides. In one or more additional examples, the predetermined sequences can correspond to nucleic acids that can be used in one or more diagnostic techniques. In one or more further examples, the predetermined sequences can correspond to nucleic acids that can be used to deliver one or more therapeutics to patients. In still other examples, the predetermined sequences can be used in one or more gene therapy procedures. The predetermined sequences can also be used in one or more biomedical procedures.

In at least some examples, the coupling of nucleotides can include successively adding nucleotides to an intermediate oligonucleotide chain until a completed oligonucleotide molecule is produced having a sequence of bases that corresponds to the predetermined sequence. In one or more instances, the addition of nucleotides can be controlled such that a given nucleotide is added to one or more specified intermediate oligonucleotide chains. For example, during one round of synthesizing oligonucleotides, the nucleotide adenine can be added to a number of intermediate oligonucleotide chains for which adenine is the next nucleotide in the predetermined sequence. The process can continue with another round of oligonucleotide synthesis causing thymine nucleotides to be added to a number of intermediate oligonucleotide chains for which thymine is the next nucleotide in the predetermined sequence. That is, nucleotides can be selectively added to intermediate oligonucleotide chains according to the predetermined oligonucleotide sequences.

Oligonucleotide molecules can be synthesized that have sequences generated according to at least one of one or more encoding schemes or one or more encoding techniques. After oligonucleotide sequence representations are generated according to one or more encoding schemes and/or techniques, oligonucleotide molecules can be synthesized and stored in one or more containers. In response to a request to retrieve at least a portion of the digital data encoded by the oligonucleotide molecules, the oligonucleotide molecules can be subjected to one or more sequencing operations. The sequencing reads generated by the one or more sequencing operations can be analyzed and decoded to retrieve the requested portion of the digital data. In situations where conventional techniques are used to encode digital data using oligonucleotides, the sequences of the oligonucleotides can have characteristics that can be problematic when the oligonucleotides are synthesized and sequenced as part of the decoding process. For example, existing techniques for encoding digital data using oligonucleotides can produce sequence representations that have repeating patterns and/or that include segments having a frequency of one or more nucleotides that is greater than a threshold frequency. In at least some examples, the threshold frequency can correspond to a frequency of the one or more nucleotides that results in a given amount of errors and/or level of inaccuracy present in the reproduced digital data. In one or more illustrative examples, sequence representations that are produced by existing techniques for encoding digital data can have segments with at least a threshold amount of GC content and/or a threshold amount of AT content. In these situations, oligonucleotides synthesized based on the sequence representations can become folded back on themselves due to self-reverse complementariness. As a result, errors can occur during the sequencing processes performed in relation to the retrieval of the digital data encoded by the oligonucleotide sequence representations. These errors can result in at least one of inaccuracies or poor reproduction of the digital data being retrieved.

Additionally, existing techniques for encoding digital data using oligonucleotides can produce oligonucleotide sequence representations that include repeating patterns of a number of nucleotides. To illustrate, oligonucleotide sequence representations generated by existing techniques to encode digital data can include segments with a threshold number of a single nucleotide repeated, a threshold number of a pair of nucleotides repeated, a threshold number of a trimer of nucleotides repeated, and so forth. In these scenarios, during the amplification processes that take place during sequencing operations, insertions and deletions can be produced in the oligonucleotide molecules present in the amplification product. Consequently, errors can be present in the portion of the digital data being retrieved.

In still other examples, a group of oligonucleotide sequence representations can have an amount of similarity in the nucleotides present at a number of positions. In one or more illustrative examples, text files can include repeated words and/or similar sentences that can result in oligonucleotide sequence representations that encode the text data having similar nucleotide sequences. In these instances, after sequencing is performed on the oligonucleotide molecules produced according to the oligonucleotide sequence representations, the grouping of similar sequencing reads to produce consensus oligonucleotide sequences can be inaccurate. For example, some sequencing reads that are grouped to determine a consensus oligonucleotide sequence may have been derived from different oligonucleotide molecules. As a result, the consensus oligonucleotide sequence may not accurately correspond to the original oligonucleotide molecules synthesized before the sequencing operations and that are based on the oligonucleotide sequence representations that encode the digital data.

In situations where a number of oligonucleotide molecules undergoing sequencing operations have one or more segments with at least a threshold amount of similarity, chimeras can be formed. To illustrate, during sequencing, replication of a given oligonucleotide molecule can be stopped in one amplification cycle and resumed in a subsequent amplification cycle such that segments of two different oligonucleotide molecules are joined to produce a chimeric oligonucleotide molecule that doesn't correspond to the full sequence of the oligonucleotide molecules contributing segments to the chimeric oligonucleotide molecule. As a result, groups of sequencing reads that are clustered to generate a consensus oligonucleotide sequence can include one or more sequencing reads that are incorrectly grouped with a given cluster. In these situations, the consensus oligonucleotide sequences can include errors, which can result in inaccuracies in the reproduction of the digital data being retrieved.

In some situations, error correction techniques can be implemented to correct errors present in the data reproduced from decoded sequencing reads. In one or more examples, redundant nucleotides can be added to nucleotide sequence representations that encode digital data. In one or more additional examples, a number of oligonucleotide molecules that include redundant data can be added into a pool of oligonucleotide molecules that encode an amount of digital data. In still other examples, existing techniques can implement procedures during the mapping of digital data (e.g., bits and/or bytes) into nucleotide sequence representations to reduce errors that may occur during the sequencing operations that are performed in conjunction with retrieval of the digital data.

In various examples, the implementations described herein minimize the problems created by existing techniques for encoding and decoding digital data using oligonucleotides and produce more accurate reproductions of digital data than when existing techniques are used. Additionally, the implementations described herein provide an improvement with respect to existing error correction techniques by resulting in more accurate reproductions of the digital data being retrieved than digital data retrieved in accordance with existing error correction techniques. In one or more examples, one or more methods, processes, techniques, schemes, or rules can be applied to nucleotide sequence representations that encode an amount of digital data. That is, rather than using existing techniques to modify the encoding of digital data using nucleotide sequence representations, implementations described herein modify the nucleotide sequence representations themselves that encode the digital data. In at least some examples, an additional encoding process can be applied to the nucleotide sequence representations that encode digital data to generate additional nucleotide sequence representations according to a transverse encoding scheme. The transverse encoding scheme can generate additional nucleotide sequence representations by identifying individual nucleotides present in individual nucleotide sequence representations and combining the individual nucleotides from the different nucleotide sequence representations to generate new nucleotide sequence representations. For example, the transverse encoding scheme can generate one or more new nucleotide sequence representation using nucleotides present at a first position of the original nucleotide sequence representations. The transverse encoding scheme can continue to be used to generate new nucleotide sequence representations using nucleotides present at other positions of the original nucleotide sequence representations. To illustrate, new nucleotide sequence representations can be generated using nucleotides present at a second position of the original nucleotide sequence representations, at a third position of the original nucleotide sequence representations, and so forth. The implementations described herein can also apply other patterns of determining individual nucleotides from individual nucleotide sequence representations to be used to generate the new nucleotide sequence representations, such as a 1-position offset between nucleotide sequence representations. In this way, rather than simply encoding digital data along the individual nucleotide sequence representations, which may preserve unwanted patterns present in the digital data, as in existing techniques, the implementations described herein encode digital data between nucleotide sequence representations and disrupt the unwanted patterns.

Further, implementations described herein can apply encryption techniques to nucleotide sequence representations based on encryption keys comprised of a segment of the nucleotide sequence representations. In one or more examples, the segment can include nucleotides that indicate a relative order in which the nucleotide sequence representations are arranged. For example, a string of characters representing digital data can be divided into a number of sections with individual sections being encoded using individual nucleotide sequence representations. In order to reproduce the digital data, the nucleotide sequence representations encoding the respective sections of the string of characters include a segment to indicate a location within the string of characters that corresponds to the digital data encoded by the respective nucleotide sequence representation. By applying one or more encryption techniques to the nucleotide sequence representations based on an encryption key present in the nucleotide sequence representations, new nucleotide sequence representations can be generated that have a more random arrangement of nucleotides that minimizes the probability of undesirable patterns of nucleotides being present in the new nucleotide sequence representations.

By implementing the techniques, processes, systems, methods, frameworks, architectures, schemes, and/or rules described herein, the number of errors present in digital data reproduced from oligonucleotide molecules is minimized. In this way, the reproduced digital data more accurately reflects the original digital data in relation to existing techniques that preserve unwanted patterns in the oligonucleotide molecules and/or implement inefficient error correction techniques.

FIG. 1 is diagram of an architecture 100 to encode digital data using oligonucleotides and to decode the digital data stored by the oligonucleotides, in accordance with one or more implementations. The architecture 100 can include input data 102. The input data 102 can include information that is to be encoded using oligonucleotides. In one or more examples, the input data 102 can include binary data stored in one or more data files. The input data 102 can correspond to digital information stored in one or more documents, one or more databases, one or more applications, one or more media files, or one or more combinations thereof.

The architecture 100 can include an oligonucleotide encoding system 104 that obtains the input data 102 The oligonucleotide encoding system 104 can be implemented by one or more computing devices 106. For example, the one or more computing devices 106 can include at least one of one or more desktop computing devices, one or more mobile computing devices, or one or more server computing device. In various examples, at least a portion of the one or more computing devices 106 can be included in a remote computing environment, such as a cloud computing environment. The oligonucleotide encoding system 104 can analyze the input data 102 and generate oligonucleotide sequence representations that encode the input data 102. To illustrate, the oligonucleotide encoding system 104 can generate encoded oligonucleotide data 108 that corresponds to the input data 102. The oligonucleotide encoding system 104 can analyze the input data 102 using one or more encoding algorithms to generate the encoded oligonucleotide data 108.

The oligonucleotide sequence representations included in the encoded oligonucleotide data 108 can correspond to DNA sequence representations, RNA sequence representations, or combinations of DNA sequence representations and RNA sequence representations. In one or more examples, one or more portions of oligonucleotide sequence representations included in the encoded oligonucleotide data 108 that correspond to DNA can include sequence representations that include the four bases found naturally occurring in DNA: cytosine (C), guanine (G), adenine (A), and thymine (T). One or more portions of oligonucleotide sequence representations included in the encoded oligonucleotide data 108 that correspond to RNA can include sequence representations that include the four bases found naturally occurring in RNA: cytosine (C), guanine (G), adenine (A), and uracil (U). In at least some examples, the oligonucleotide sequence representations included in the encoded oligonucleotide data 108 can include single stranded oligonucleotide sequence representations. In one or more additional examples, the oligonucleotide sequence representations included in the encoded oligonucleotide data 108 can include double stranded sequence representations. In one or more further examples, the oligonucleotide sequence representations included in the encoded oligonucleotide data 108 can include a combination of single stranded sequence representations and double stranded sequence representations.

In one or more examples, the oligonucleotide encoding system 104 can perform a first encoding process that encodes the digital data included in the input data 102 as one or more strings of characters that include representations of nucleotides included in at least one of DNA or RNA. For example, various combinations of binary digits can be represented by at least one of A, T, G, C, or U. The oligonucleotide encoding system 104 can then perform one or more second encoding processes to produce the encoded oligonucleotide data 108. In at least some examples, a second encoding process can include generating nucleotide sequence representations with positions that correspond to a schema with respect to the one or more strings of characters generated by the first encoding process.

In various examples, the schema can indicate that oligonucleotides encoding the input data 102 can have a specified length and that for a given number of consecutive positions of a string of characters representing the digital data 102, a single character from the string will be included in a single oligonucleotide sequence representation. To illustrate, in scenarios where oligonucleotide sequence representations having 100 nucleotides are used to represent the digital data 102, for every 100 characters of the string of characters generated from the digital data 102, one out of the 100 characters will be allocated to an individual position of a representation of the oligonucleotides. In one or more illustrative examples, a string of 1000 characters can be generated using a first encoding process to represent at least a portion of the digital data 102. The string of 1000 characters can then be divided into 10 groups of characters with each group having 100 characters. Continuing with this example, a second encoding process can determine that a first character included in a first group of characters can be included in a first position of a first oligonucleotide sequence representation, a second character included in a second group characters can be included in a first position of a second oligonucleotide sequence representation, and a third character included in a third group characters can be included in a first position of a third oligonucleotide sequence representation. In response to the first position of the oligonucleotide sequence representations being filled by one character from each group, a second position of the oligonucleotide sequence representations can then be filled with a single character from each group of characters. The second encoding process can continue until the 100 individual positions of each oligonucleotide sequence representation have been filled using a single character from each group of characters. In these examples, the encoded oligonucleotide data 108 can comprise the oligonucleotide sequence representations generated by the second encoding process.

In one or more additional examples, the oligonucleotide encoding system 104 can determine locations in the oligonucleotide sequence representations for individual nucleotides of the groups of characters based on a schema that implements an offset for the positions of the nucleotides. To illustrate, in one or more scenarios where the offset is a single position, the oligonucleotide encoding system 104 can determine that a first nucleotide included in a first group of characters is located at a first position of a first oligonucleotide representation, that a first nucleotide included in a second group of characters is located at a second position of a second oligonucleotide representation, and that a first nucleotide included in a third group of characters is located at a third position of a third oligonucleotide representation. Continuing with this example, the oligonucleotide encoding system 104 can determine that a second oligonucleotide included in the first group of characters can be located at a second position of the first oligonucleotide sequence representation, a second oligonucleotide of the second group of characters can be located at a third position of a second oligonucleotide sequence representation, and that a second oligonucleotide of the third group of characters can be located at a fourth position of a third oligonucleotide sequence representation.

In one or more additional examples, a second encoding process can include generating nucleotide sequence representations using one or more encryption processes based on an encryption key that corresponds to an individual oligonucleotide sequence representations. For example, a string of characters generated as part of a first encoding process to represent the input data 102 can be divided into a number of groups. In various examples, individual groups can have a same number of characters, while in other examples, individual groups can have different numbers of characters. The individual groups can correspond to individual oligonucleotide sequence representations. The second encoding process can determine an identifier for the individual oligonucleotide sequence representations. In at least some examples, the identifier for the individual oligonucleotide representations can uniquely identify the individual oligonucleotide representations and indicate an order of the individual oligonucleotide sequence representations within the string of characters produced by the first encoding process. One or more encryption processes can be applied to the string of characters included in the individual oligonucleotide sequence representations using the identifier of the individual oligonucleotide sequence representations as an encryption key to generate a modified string of characters that corresponds to a modified version of the individual oligonucleotide sequence representations. In these scenarios, the encoded oligonucleotide data 108 can include the modified versions of the individual oligonucleotide sequence representations generated by implementing the one or more encryption processes using the respective encryption keys.

The architecture 100 can include an oligonucleotide synthesizer apparatus 110 that synthesizes oligonucleotide molecules 112 based on the encoded oligonucleotide data 108. The oligonucleotide synthesizer apparatus 110 can implement synthesis of oligonucleotide molecules using nucleoside phosphoramidites. The synthesis of oligonucleotide molecules by the oligonucleotide synthesizer apparatus 110 can add nucleoside phosphoramidite building blocks in a 3' to 5' direction to intermediate oligonucleotide chains. In one or more examples, the nucleoside phosphoramidite building blocks can be added to intermediate oligonucleotide chains in an order that corresponds to the oligonucleotide sequence representations included in the encoded oligonucleotide data 108. The nucleoside phosphoramidites used to synthesize the oligonucleotide molecules 112 can be included in nucleoside building block solutions 114. In various examples, the nucleoside building block solutions 114 can include multiple solutions with individual solutions including a single nucleoside phosphoramidite. For example, the nucleoside building block solutions 114 can include a first solution that includes deoxyadenosine phosphoramidites, a second solution that includes deoxythymidine phosphoramidites, a third solution that includes deoxyguanosine phosphoramidites, and a fourth solution that includes deoxycytidine phosphoramidites. In situations where the oligonucleotides 112 include RNA sequences, the nucleoside building block solutions 114 can include deoxyuridine phosphoramidites. The nucleoside building block solutions 114 can be solutions that also include at least one of a buffer or a salt.

The architecture 100 can also include reaction solutions 116. The reaction solutions 116 can cause one or more chemical reactions to take place within the oligonucleotide synthesizer apparatus to produce the oligonucleotide molecules 112. For example, the reaction solutions 116 can include a deblocking solution that can include compounds that facilitate the removal of protecting groups from intermediate oligonucleotide chains. Additionally, the reaction solutions 116 can include one or more acetylation solutions to cap unreacted 5' hydroxyl groups after the addition of nucleoside phosphoramidite building blocks to intermediate oligonucleotide chains. The capping step can prevent intermediate oligonucleotide chains that did not add a nucleoside phosphoramidite building blocks in a synthesis cycle from participating in additional synthesis reactions that may result in a deletion error. The one or more acetylation solutions can include acetic anhydride, N-methyl imidazole, tetrahydrofuran, and pyridine. Further, reaction solutions 116 can include one or more oxidation solutions that can convert the phosphite group of the nucleoside phosphoramidite building blocks to a phosphate group that links the nucleotides of the intermediate oligonucleotide chains. In at least some examples, the one or more oxidation solutions can include iodine, water, and pyridine.

Each cycle of the oligonucleotide synthesis process can cause a single nucleotide to be added to intermediate oligonucleotide chains. The order of the nucleotides added to the intermediate oligonucleotide chains is based on the oligonucleotide sequence representations included in the encoded oligonucleotide data 108. In one or more illustrative examples, when a next nucleotide to be added to one or more intermediate oligonucleotide chains is adenine, a cycle of the oligonucleotide synthesis process can be performed with a deoxyadenosine phosphoramidite solution and when a next nucleotide to be added to one or more intermediate oligonucleotide chains is thymine, a cycle of the oligonucleotide synthesis process can be performed with a deoxythymidine phosphoramidite solution. Additionally, when a next nucleotide to be added to one or more intermediate oligonucleotide chains is guanine, a cycle of the oligonucleotide synthesis process can be performed with a deoxyguanosine phosphoramidite solution and when a next nucleotide to be added to one or more intermediate oligonucleotide chains is cytosine, a cycle of the oligonucleotide synthesis process can be performed with a deoxycytidine phosphoramidite solution.

After synthesis of oligonucleotide chains by the oligonucleotide synthesizer apparatus 110 is complete and protecting groups are removed, the completed oligonucleotide chains can be stored under conditions that minimize degradation of the oligonucleotide molecules 112. For example, the oligonucleotide molecules 112 can be stored at temperatures from about −10° C. to −80° C. or from −20° C. to −70° C. in a slightly basic solution. To illustrate, the oligonucleotide molecules 112 can be stored in a solution having a pH from about 7.8 to about 8.2 that includes at least one of Tris(hydroxymethyl)aminomethane hydrochloride or Ethylenediaminetetraacetic acid (EDTA). In one or more additional examples, the oligonucleotide molecules 112 can undergo one or more drying processes and be stored at temperatures from about 10° C. to about 25° C.

The storage of the oligonucleotide molecules 112 in a suitable environment enables the data encoded by the oligonucleotide molecules 112 to be stored until a request is received to retrieve the encoded data. To retrieve data encoded by at least a portion of the oligonucleotide molecules 112, the portion of the oligonucleotide molecules 112 that corresponds to the data being retrieved are provided to a sequencing apparatus 118. The sequencing apparatus 118 can perform one or more sequencing operations to generate sequencing data 120. The sequencing data 120 can include sequencing reads that correspond to the nucleotide sequences of at least a portion of the oligonucleotide molecules 112. The sequencing apparatus 118 can implement one or more next generation sequencing techniques. Next generation sequencing techniques can include post-Sanger, high throughput sequencing techniques that sequence millions of nucleotide fragments in parallel. In various examples, the sequencing apparatus 118 can implement other sequencing techniques, such as Sanger sequencing, nanopore sequencing, or single molecular real-time sequencing.

The sequencing data 120 can be analyzed by an oligonucleotide decoding system 122 that is implemented by one or more computing devices 124. The oligonucleotide decoding system 122 can implement one or more computational algorithms to generate decoded oligonucleotide data 126 from the sequencing data 120. For example, the oligonucleotide decoding system 122 can analyze sequencing reads to determine at least one of the bits or bytes encoded by the respective sequencing reads to produce the decoded oligonucleotide data 126. In one or more examples, the decoded oligonucleotide data 126 can be assembled into a data file that can be read by a computing device. In one or more illustrative examples, the decoded oligonucleotide data 126 can be used to generate a portion of a database that corresponds to at least a portion of the input data 102. In one or more additional examples, information decoded using the oligonucleotide decoding system 122 can be displayed via one or more user interfaces. Further, the information decoded by the oligonucleotide decoding system 122 can be modified via one or more client applications executed by one or more computing devices to produce modified data. Information included in the modified data can be stored by one or more computer-readable media and/or by encoding using the oligonucleotide encoding system 104.

The oligonucleotide decoding system 122 can implement one or more decoding processes to determine digital information that is represented by sequencing reads corresponding to the oligonucleotide molecules 112. In one or more examples, the oligonucleotide decoding system 122 can analyze sequencing reads included in the sequencing data 120 to determine oligonucleotide sequence representations that correspond to the sequencing reads. The one or more decoding processes implemented by the oligonucleotide decoding system 122 to analyze the sequencing data 120, can be based on the encoding processes implemented by the oligonucleotide encoding system 104 to generate the encoded oligonucleotide data 108. For example, in scenarios where the oligonucleotide encoding system 104 generates the encoded oligonucleotide data 108 according to a schema, the oligonucleotide decoding system 122 can analyze the sequencing reads included sequencing data 120 in a manner that reverses the schema used to generate a number of groups of characters. The oligonucleotide decoding system 122 can then arrange the groups of characters according to a given order. The order can correspond to the location of each group of characters within the original string of characters generated by the oligonucleotide encoding system 104 using the first encoding process to encode the input data 102. In various examples, the oligonucleotide decoding system 122 can analyze the ordered groups of characters according to a nucleotide to numerical code mapping and generate an additional string of characters that corresponds to the digital data being retrieved.

Additionally, in situations where the oligonucleotide encoding system 104 generates the encoded oligonucleotide data 108 by implementing one or more encryption processes using a key, the oligonucleotide decoding system 122 can analyze the sequencing reads included in the sequencing data 120 by implementing a decryption process that uses the key that was used to encrypt the oligonucleotide sequence representations. In this way, the oligonucleotide decoding system 122 can generate a number of groups of characters that correspond to the decrypted sequencing reads. The oligonucleotide decoding system 122 can arrange the groups of characters according to a given order. The order can correspond to the location of each group of characters within the original string of characters generated by the oligonucleotide encoding system 104 using the first encoding process to encode the input data 102. In one or more examples, the oligonucleotide decoding system 122 can then analyze the ordered groups of characters according to a nucleotide-to-numerical code mapping and generate an additional string of characters that corresponds to the digital data being retrieved.

Figure 2:
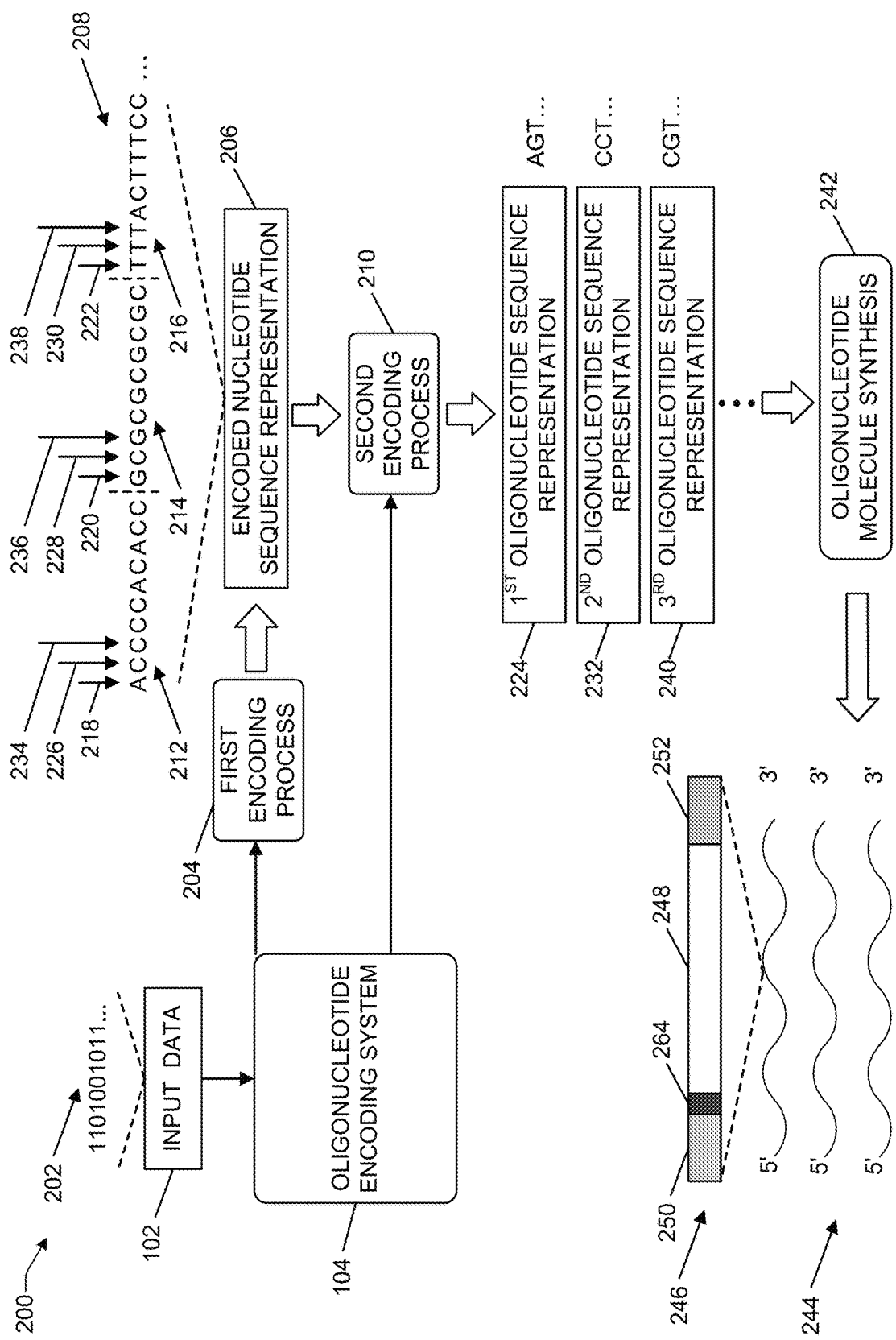
FIG. 2 is a diagram of a framework to encode digital data using oligonucleotides according to multiple encoding schemes, in accordance with one or more implementations.

FIG. 2 is a diagram of a framework 200 to encode digital data using oligonucleotides according to multiple encoding processes, in accordance with one or more implementations. The framework 200 can include the oligonucleotide encoding system 104. The oligonucleotide encoding system 104 can analyze the input data 102. The input data 102 can include digital data that has been generated by one or more applications executed by one or more computing devices. In one or more examples, the input data 102 can be represented according to one or more positional number systems. In at least some examples, the input data 102 can include a first string of characters 202, such as a string of alphanumeric characters that represent the digital data. In one or more illustrative examples, a binary number system can be used to represent the input data 102. In these scenarios, the input data 102 can include a number of bits and a number of bytes. In one or more additional illustrative examples, the input data 102 can be represented by a hexadecimal number system. In one or more further illustrative examples, the input data 102 can be represented by an octal number system. In still other illustrative examples, the input data 102 can be represented by a decimal number system.

The oligonucleotide encoding system 104 can implement a first encoding process 204 to generate an encoded nucleotide sequence representation 206 from the first string of characters 202. In one or more examples, the first encoding process 204 can transform the first string of characters 202 to a second string of characters 208 with individual characters of the second string of characters 208 being represented by nucleotides included in at least one of DNA or RNA. In this way, the first encoding process 204 can generate the encoded nucleotide sequence representation 206 to include a string of characters that includes one or more A's, one or more G's, one or more C's, one or more T's, and, in cases where the encoded nucleotide sequence representation 206 corresponds to RNA, one or more U's instead of one or more T's. The first encoding process 204 can include transforming combinations of characters included in first string of characters 202 to one or more characters included in DNA and/or RNA sequences to generate the encoded nucleotide representation 206 according to a first encoding scheme. In one or more illustrative examples, the oligonucleotide encoding system 104 can implement the first encoding process 204 to transform a 00 combination in the first string of characters 202 as an A in the second string of characters 208, a 01 combination in the first string of characters 202 as a T in the second string of characters 208, a 10 combination in the first string of characters 202 as a G in the second string of characters 208, and a 11 combination in the first string of characters 202 as a C in the second string of characters 208. Although an example first encoding scheme has been described above as an illustrative example, a number of different encoding schema can be implemented by the oligonucleotide encoding system 104 in the first encoding process 204 to generate the encoded nucleotide sequence representation 206 from the input data 102.

The oligonucleotide encoding system 104 can also implement a second encoding process 210. The second encoding process 210 can include applying a second encoding scheme to the encoded nucleotide sequence representation 206. In one or more examples, the second encoding process 210 can be implemented by the oligonucleotide encoding system 104 to generate additional oligonucleotide sequence representations from the encoded nucleotide sequence representation 206. In various examples, the second encoding process 210 can include determining a number of groups of characters based on the second string of characters 208 with each group of characters corresponding to an individual oligonucleotide sequence representation. In at least some examples, the second encoding process 210 can include dividing the encoded nucleotide sequence representation 206 into a number of individual oligonucleotide sequence representations that encode the digital data. In one or more illustrative examples, the second encoding process 210 can include generating at least 50 oligonucleotide sequence representations from the encoded nucleotide sequence representation 206 to encode the digital data, generating at least 100 oligonucleotide sequence representations from the encoded nucleotide sequence representation 206 to encode the digital data, generating at least 200 oligonucleotide sequence representations from the encoded nucleotide sequence representation 206 to encode the digital data, generating at least 300 oligonucleotide sequence representations from the encoded nucleotide sequence representation 206 to encode the digital data, generating at least 400 oligonucleotide sequence representations from the encoded nucleotide sequence representation 206 to encode the digital data, generating at least 500 oligonucleotide sequence representations from the encoded nucleotide sequence representation 206 to encode the digital data, generating at least 600 oligonucleotide sequence representations from the encoded nucleotide sequence representation 206 to encode the digital data, generating at least 700 oligonucleotide sequence representations from the encoded nucleotide sequence representation 206 to encode the digital data, generating at least 800 oligonucleotide sequence representations from the encoded nucleotide sequence representation 206 to encode the digital data, generating at least 900 oligonucleotide sequence representations from the encoded nucleotide sequence representation 206 to encode the digital data, or generating at least 1000 oligonucleotide sequence representations from the encoded nucleotide sequence representation 206 to encode the digital data.

In one or more examples, the oligonucleotide encoding system 104 can determine a number of groups of characters based on the second string of characters 208 such that individual groups of characters have at least a minimum number of characters. Additionally, the oligonucleotide encoding system 104 can determine a number of groups of characters based on the second string of characters 208 such that individual groups of characters have no greater than a maximum number of characters. Further, the oligonucleotide encoding system 104 can determine a number of groups of characters based on at least a portion of the second string of characters 208 such that individual groups of characters have a same number of characters. In one or more illustrative examples, the oligonucleotide sequence representations can individually include at least 50 nucleotides, at least 100 nucleotides, at least 250 nucleotides, at least 500 nucleotides, at least 750 nucleotides, at least 1000 nucleotides, at least 2000 nucleotides, at least 3000 nucleotides, at least 4000 nucleotides, at least 5000 nucleotides, at least 6000 nucleotides, at least 7000 nucleotides, at least 8000 nucleotides, at least 9000 nucleotides, or at least 10,000 nucleotides. In various examples, the oligonucleotide sequence representations can include from about 50 nucleotides to about 10,000 nucleotides, from about 100 nucleotides to about 8000 nucleotides, from about 200 nucleotides to about 5000 nucleotides, from about 100 nucleotides to about 500 nucleotides, from about 250 nucleotides to about 750 nucleotides, from about 500 nucleotides to about 2000 nucleotides, from about 1000 nucleotides to about 5000 nucleotides, or from about 5000 nucleotides to about 10,000 nucleotides.

In the illustrative example of FIG. 2, the oligonucleotide encoding system 104 can generate three groups of characters based on a portion of the second string of characters 208. For example, the oligonucleotide encoding system 104 can identify a first group of characters 212, a second group of characters 214, and a third group of characters 216 based on a portion of the second string of characters 208. The first group of characters 212, the second group of characters 214, and the third group of characters 216 can include a same number of characters of the second string of characters 208.

The oligonucleotide encoding system 104 can implement the second encoding process 210 according to one or more schema where a nucleotide present at a given position of the individual groups 212, 214, 216 is located at a specified position of additional oligonucleotide sequence representations generated by the oligonucleotide encoding system 104. In the illustrative example of FIG. 2, a nucleotide present at a first position 218 of the first group 212 can be located at a first position of a first oligonucleotide sequence representation 224, a nucleotide present at a first position 220 of the second group 214 can be located at a second position of the first oligonucleotide sequence representation 224, and a nucleotide present at a first position 230 of the third group 216 can be located at a third position of the first nucleotide sequence representation 224. In this way, the first three nucleotides of the first oligonucleotide sequence representation 224 can be AGT.

Additionally, a nucleotide present at a second position 226 of the first group 212 can be located at a first position of a second oligonucleotide sequence representation 232, a nucleotide present at a second position 228 of the second group 214 can be located at a second position of the second oligonucleotide sequence representation 232, and a nucleotide present at a second position of the third group 216 can comprise a portion of a second oligonucleotide sequence representation 232. As a result, the first three nucleotides of the second oligonucleotide sequence representation 232 can be CGT. Further, a nucleotide present at a third position 234 of the first group 212 can be located at a first position of a third oligonucleotide sequence representation 240, a nucleotide present at a second position 236 of the second group 214 can be located at a second position of the third oligonucleotide sequence representation 240, and a nucleotide present at a third position 238 of the third group 216 can be located at a third position of the third oligonucleotide sequence representation 240. Accordingly, the first three nucleotides of the third nucleotide sequence representation 240 can include CGT.

In various examples, the second encoding process 210 can continue until the oligonucleotide encoding system 104 has determined locations in the oligonucleotide sequence representations 224, 232, 240 for additional nucleotides included in the groups 212, 214, 216 by determining nucleotides from additional groups generated from the second string of characters 208. For example, a fourth, group, fifth group, and the like can be generated from the second string of characters 208 and nucleotides included in these groups can be added to the oligonucleotide sequence representations 224, 232, 240. In addition, oligonucleotide sequence representations in addition to oligonucleotide sequence representations 224, 232, 240 can be generated according to the second encoding process 210 using nucleotides located at additional positions of the groups of characters generated from the second string of characters 208.

Although the illustrative example of FIG. 2 is directed to the oligonucleotide encoding system 104 implementing the second encoding process 210 according to an example scheme, the oligonucleotide encoding system 104 can implement the second encoding process 210 according to one or more additional schema. To illustrate, the oligonucleotide encoding system 104 can determine that a nucleotide present at the first position 218 of the first group 212 is located at a first position of the first sequence representation 224, a nucleotide present at a second position 226 of the first group 212 is located at a second position of the second sequence representation 232, and a nucleotide present at a third position 234 of the first group 212 is located at a third position of the third sequence representation 240. In this way, the oligonucleotide encoding system 104 can implement the second encoding process 210 using a scheme that includes a positional offset with respect to the location of a nucleotide in the groups 212, 214, 216 and the location of the nucleotide in the sequence representations 224, 232, 240.

The framework 200 can also include oligonucleotide molecule synthesis 242 that causes oligonucleotides 244 to be physically synthesized according to the oligonucleotide sequence representations generated by the second encoding process 210. For example, a first oligonucleotide molecule can be synthesized that corresponds to the first oligonucleotide sequence representation 224, a second oligonucleotide molecule can be synthesized that corresponds to the second oligonucleotide sequence representation 232, and a third oligonucleotide molecule can be synthesized that corresponds to the third oligonucleotide sequence representation 240. In one or more illustrative examples, the oligonucleotide sequence representations generated by the second encoding process 210 can correspond to payloads of the oligonucleotide molecules because those portions of the oligonucleotide molecules encode a portion of the input data 102. In various examples, the oligonucleotide molecules 244 can also include primers that were added as part of the oligonucleotide molecule synthesis 242. The primers can be used during sequencing operations to identify copies of the oligonucleotide molecules 244 produced during sequencing operations. Additionally, the oligonucleotide molecules 244 can include a number of nucleotides that indicate an order of the payload within the encoded nucleotide sequence representation 206. An illustrative oligonucleotide sequence 246 that corresponds to the oligonucleotides 244 can include a payload 248 that includes nucleotides that corresponds to oligonucleotide sequence representations that encode an amount of the input data 102, such as the example sequence representations 224, 232, 240. Further, the illustrative oligonucleotide sequence 246 can include a 5' primer 250 and a 3' primer 252. The illustrative oligonucleotide sequence 246 can also include an ordering sequence 254. In at least some examples, the ordering sequence 254 can indicate a group of the encoded nucleotide sequence representation 206 that corresponds to the payload 248. In one or more examples, the ordering sequence 254 can be used during the decoding process to reproduce the encoded nucleotide sequence representation 206.

Figure 3:
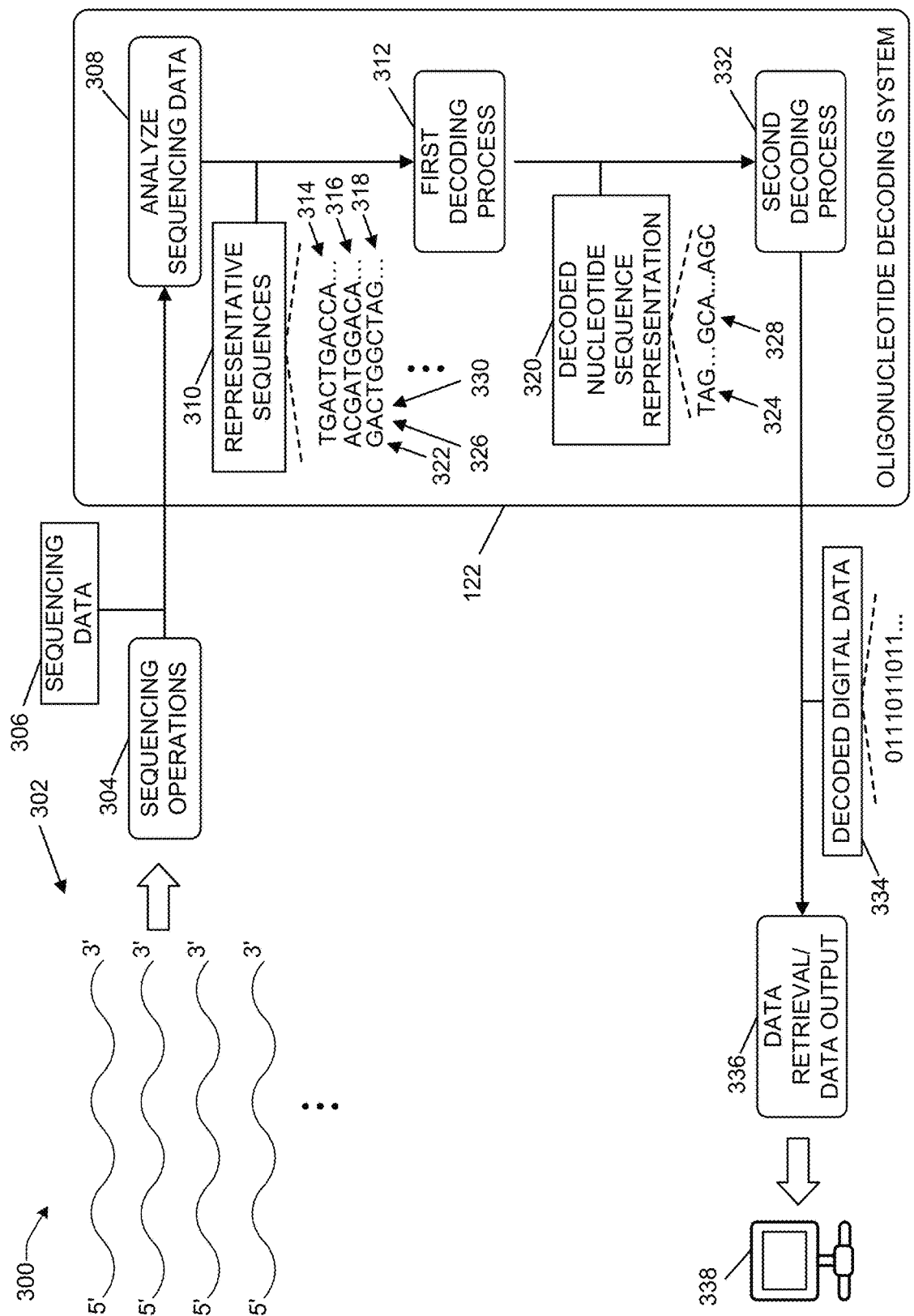
FIG. 3 is a diagram of a framework to decode digital data that has been encoded using oligonucleotides according to multiple encoding processes, in accordance with one or more implementations.

FIG. 3 is a diagram of a framework 300 to decode data that has been encoded using oligonucleotides according to multiple encoding processes, in accordance with one or more implementations. The framework 300 can include oligonucleotide molecules 302. In one or more examples, at least a portion of the oligonucleotide molecules 302 can include nucleotide sequences that correspond to digital data that has been encoded using oligonucleotides according to one or more encoding processes. In one or more additional examples, the oligonucleotide molecules 302 can include additional nucleotide sequences that corresponds to one or more primers. The oligonucleotide molecules 302 can also include nucleotide sequences that indicate an order in which the respective sequences of the oligonucleotides 302 are to be arranged during one or more decoding processes. In one or more illustrative examples, the oligonucleotide molecules 302 can correspond to the oligonucleotide molecules 244 described in relation to FIG. 2.

Sequencing operations 304 can be performed as part of the framework 300. The sequencing operations 304 can produce many copies of the individual oligonucleotide molecules 302. For example, the sequencing operations 304 can produce an amplification product that includes thousands, tens of thousands, up to millions of copies of individual oligonucleotide molecules 302. In one or more illustrative examples, the sequencing operations 304 can include high-throughput sequencing operations. In one or more illustrative examples, the sequencing operations 304 can be performed according to techniques described in "High-Throughput Sequencing Technologies" by Jason A. Reuter et al., Mol. Cell. 2015 May 21; 58) 4); 586-597.

The sequencing operations 304 can generate sequencing data 306. The sequencing data 306 can include alphanumeric sequence representations of the oligonucleotide molecules 302 included in an amplification product produced by the sequencing operations 304. For example, the sequencing data 306 can include, for individual oligonucleotide molecules included in the amplification product, data that corresponds to a string of characters that represent the respective chains of nucleotides that correspond to the individual oligonucleotide molecules of the amplification product. In at least some examples, the sequencing data 306 can include sequencing reads. An individual sequence representation included in the sequencing data 306 can be referred to herein as a "read" or a "sequencing read." The sequencing reads included in the sequencing data 306 can individually include a first portion that corresponds to digital data encoded by a nucleotide sequence, one or more second portions that correspond to one or more primers, and a third portion that corresponds to a nucleotide sequence order marker.

The sequencing data 306 can be stored in one or more data files. For example, the sequencing data 306 can be stored in a FASTQ file that comprises a text-based sequencing data file format storing raw sequence data and quality scores. In one or more additional examples, the sequencing data 306 can be stored in a data file according to a binary base call (BCL) sequence file format. In one or more further examples, the sequencing data 306 can be stored in a BAM file. In one or more examples, the sequencing data 306 can comprise at least about one gigabyte (GB), at least about 2 GB, at least about 3 GB, at least about 4 GB, at least about 5 GB, at least about 8 GB, or at least about 10 GB.

In various examples, the framework 300 can include the oligonucleotide decoding system 122. The oligonucleotide decoding system 122 can perform a number of operations to analyze and transform the sequencing data 306 to digital data. The digital data can be the subject of a request to retrieve the digital data for use by one or more computing devices. In one or more examples, the oligonucleotide decoding system 122 can analyze the sequencing data 306 at operation 308. The sequencing data 306 can be analyzed prior to the implementation of one or more decoding processes by the oligonucleotide decoding system 122. In at least some examples, the sequencing data 306 can undergo one or more preprocessing operations before being subjected to one or more decoding operations. In one or more illustrative examples, the oligonucleotide decoding system 122 can, at operation 308, determine an order for the sequencing reads included in the sequencing data 306. For example, the oligonucleotide decoding system 122 can analyze the sequencing data 306 to determine segments of nucleotides within the sequencing reads that indicate a location of a payload portion of the individual sequencing reads within a string of characters, where the string of characters represents encoded, such as the first string of characters 208 described with respect to FIG. 2. To illustrate, the oligonucleotide decoding system 122 can determine that a location of a payload portion of a sequencing read within an encoded nucleotide sequence representation based on a section of the sequencing read that includes a code or other indicator of the location of the payload portion of the sequencing read. The oligonucleotide decoding system 122 can then produce one or more additional character strings that include an ordered combination of sequencing reads included in the sequencing data 306.

In one or more illustrative examples, the oligonucleotide decoding system 122 can analyze the sequencing data 306 to determine representative sequences 310. The representative sequences 310 can correspond to individual oligonucleotide sequence representations that represent a number of sequencing reads included in the sequencing data 306. For example, the oligonucleotide decoding system 122 can determine groups of sequencing reads included in the sequencing data 306. The sequencing reads included in an individual group can have at least a threshold amount of homology with respect to one another. To illustrate, the sequencing reads included in an individual group of sequencing reads can have at least about 90% homology with respect to one another, at least about 95% homology with respect to one another, at least about 97% homology with respect to one another, at least about 99% homology with respect to one another, or at least about 99.5% homology with respect to one another. The amount of homology between a given sequence representation and a portion of a reference sequence can be determined using BLAST programs (basic local alignment search tools) and Power-BLAST programs (Altschul et al., J. Mol. Biol., 1990, 215, 403-410; Zhang and Madden, Genome Res., 1997, 7, 649-656) or by using the Gap program (Wisconsin Sequence Analysis Package, Genetics Computer Group, University Research Park, Madison Wis.), using default settings, which uses the algorithm of Needleman and Wunsch (J. Mol. Biol. 48; 443-453 (1970)). The amount of homology between a sequence representation and a portion of the reference sequence can also be determined using a Burrows-Wheeler aligner (Li, H., & Durbin, R. (2009). Fast and accurate short read alignment with Burrows-Wheeler transform. *Bioinformatics*, 25 (14), 1754-1760).

In at least some examples, the representative sequences 310 can correspond to sequencing reads included in the sequencing data 306 that correspond to a number of copies of individual nucleotide molecules 302. In one or more additional examples, the oligonucleotide decoding system 122 can perform one or more operations to order the representative sequences 310 based on portions of the representative sequences 310 that indicate the order of the individual representative sequences 310 within an encoded nucleotide sequence representation that corresponds to an amount of digital data.

The oligonucleotide decoding system 122 can perform a first decoding process 312 with respect to the representative sequences 310. After the representative sequences 310 have been ordered, the first decoding process 312 can include aligning the representative sequences 310. In one or more illustrative examples, the representative sequences 312 can include a first ordered and aligned representative sequence 312, a second ordered and aligned representative sequence 314, and a third ordered and aligned representative sequence 316. In various examples, the representative sequences 310 can include hundreds, thousands, tens of thousands, up to hundreds of thousands of ordered and aligned representative sequences or more.

As used herein, "alignment" or "aligning" refers to arranging nucleotide sequences such that individual consecutive positions of the individual nucleotide sequences correspond to one another. For example, nucleotide sequences can be aligned such that the first nucleotide position of each nucleotide sequence correspond to one another, the second nucleotide position of each nucleotide sequence correspond to one another, the third nucleotide position of each nucleotide sequence correspond to one another, and so forth. In one or more illustrative examples, sequence representations can be "aligned" when at least a threshold number of consecutive positions of the sequence representations correspond to one another, such as at least about 90% of consecutive positions of the sequence representations correspond to one another, at least about 92% of consecutive positions of the sequence representations correspond to one another, at least about 95% of consecutive positions of the sequence representations correspond to one another, at least about 98% of consecutive positions of the sequence representations correspond to one another, at least about 99% of consecutive positions of the sequence representations correspond to one another, at least about 99.5% of consecutive positions of the sequence representations correspond to one another, or at least about 99.9% of consecutive positions of the sequence representations correspond to one another.

In one or more examples, the first decoding process 312 can include performing one or more operations with respect to the ordered and aligned representative sequences 310 that are based on the operations used to encode the digital data being retrieved. For example, the first decoding process 312 can include applying at least one of one or more rules or one or more schemes based on at least one of one or more additional rules or one or more additional schemes that were used to encode the digital data being retrieved. In various examples, the first decoding process 312 can generate a decoded nucleotide sequence representation 320. The decoded nucleotide sequence representation 320 can include a string of characters that corresponds to the encoded nucleotide sequence representation 206 described with respect to FIG. 2. In one or more illustrative examples, the encoded nucleotide sequence representation 320 can include a string of characters with individual characters of the decoded nucleotide sequence representation 320 comprising a character that represents a nucleotide present in at least one of DNA or RNA. In one or more scenarios, the decoded nucleotide sequence representation 320 can correspond to the encoded nucleotide sequence representation 206 with one or more differences. The one or more differences can be present due to one or more errors that occurred during the sequencing operations 304. In one or more implementations, the first decoding process 312 can include performing one or more error correction processes with respect to the representative sequences 310. In at least some examples, the number of errors present in the decoded nucleotide sequence representation 320 are minimized due to the one or more rules and/or the one or more schemas implemented with respect to the second encoding process 210 described with respect to FIG. 2 and the first decoding process 312.

In one or more additional examples, the first decoding process 312 can include determining individual nucleotides present at individual positions of the representative sequences 310 to determine nucleotides present at individual locations of the decoded nucleotide sequence representation 320. In one or more illustrative examples, the first decoding process 312 can include determining a first number of nucleotides located at a first position 322 of the ordered and aligned representative sequences 314, 316, 318 to determine a first portion 324 of the decoded nucleotide sequence representation 320. For example, the first portion 324 of the decoded nucleotide sequence representation 320 can comprise TAG obtained from the nucleotides present at the first position 322 of the ordered and aligned representative sequences 314, 316, 318. The first decoding process 312 can continue determining nucleotides present at the first position 322 for additional ordered and aligned representative sequences until the nucleotides present at the first position 322 for each of the ordered and aligned representative sequences have been added sequentially to the decoded nucleotide sequence representation 320. The first decoding process 312 can continue by determining a second number of nucleotides present at a second position 326 of the ordered and aligned representative sequences 314, 316, 318 to determine a second portion 328 of the decoded nucleotide sequence representation 320. To illustrate, the second portion 328 of the decoded nucleotide sequence representation 320 can comprise GCA obtained from nucleotide present at the second position 326 of the ordered and aligned representative sequences 314, 316, 318. The first decoding process 312 can continue determining nucleotides present at the second position 326 for each of the ordered and aligned representative sequences until the nucleotides present at the second position 326 for each of the ordered and aligned representative sequences have been added sequentially to the decoded nucleotide sequence representation 320. Further, the first decoding process 312 can continue moving sequentially along the positions of the ordered and aligned representative sequences until the nucleotides present at the individual positions of the individual ordered and aligned representative sequences have been added to the decoded nucleotide sequence representation 320. In this way, the first decoding process 312 can include reversing a transverse encryption scheme to determine an arrangement of nucleotides of the representative sequences 310 that comprise the decoded nucleotide sequence representation 320.

In one or more further examples, the first decoding process 312 can implement a different set of one or more rules or one or more schemes to generate the decoded nucleotide sequence representation 320. For example, the first decoding process 312 can include determining a first nucleotide of the decoded nucleotide sequence representation 320 by determining a first nucleotide at the first position 322 of the first ordered and aligned representative sequence 314, determining a second nucleotide of the decoded nucleotide sequence representation 320 by determining a second nucleotide at the second position 326 of the second ordered and aligned representative sequence 316, and determining a third nucleotide of the decoded nucleotide sequence representation 326 by determining a third nucleotide at a third position 330 of the third ordered and aligned representative sequence 318. The first decoding process 312 can continue adding nucleotides to the decoded nucleotide sequence representation 320 according to a one position offset until one nucleotide has been added to the decoded nucleotide sequence representation 320 from each position of the ordered and aligned representative sequences. The first decoding process 312 can then add a nucleotide from the second position 326 of the first ordered and aligned representative sequence 314 to the decoded nucleotide sequence representation 320 and an additional nucleotide from the third position 330 of the second ordered and aligned representative sequence to the decoded nucleotide sequence representation 320. The first decoding process 312 can then continue adding nucleotides to the decoded nucleotide sequence representation 320 according to a one position offset until each nucleotide of the representative sequences 310 have been added to the decoded nucleotide sequence representation 320.

In various examples, the first decoding process 312 can include implementing a different offset with respect to positions of the ordered and aligned representative sequences to generate the decoded nucleotide sequence representation 320. In one or more illustrative examples, the first sequence encoding 312 can implement a 1-position offset, a 2-position offset, a 3-position offset, a 4-position offset, a 5-position offset, a 6-position offset, a 7-position offset, an 8-position offset, a 9-position offset, a 10-position offset, a 12-position offset, a 15-position offset, a 20-position offset, or a 25-position offset with respect to adding nucleotides of the ordered and aligned representative sequences to generate the decoded nucleotide sequence representation 320. In at least some examples, additional patterns can be implemented by the first decoding process 312 to add nucleotides from the ordered and aligned representative sequences to generate the decoded nucleotide sequence representation 320.

The oligonucleotide decoding system 122 can also implement a second decoding process 332 with respect to the decoded nucleotide sequence representation 320. The second decoding process 332 can generate decoded digital data 334 based on the decoded nucleotide sequence representation 320. In one or more examples, one or more combinations of nucleotides can correspond to one or more additional combinations of alphanumerical representations that correspond to digital data. In this way, the second decoding process 332 can transform the decoded nucleotide sequence representation 320 into the decoded digital data 334. In various examples, the second decoding process 332 can implement the one or more rules and/or one or more schemes related to those used in the first encoding process 204 described with respect to FIG. 2.

The framework 300 can also include one or more data retrieval and/or one or more data output operations 336. The one or more data retrieval and/or one or more data output operations 336 can include one or more computing devices 338 accessing the decoded digital data 334. The one or more computing devices 338 can include one or more mobile computing devices, one or more laptop computing devices, one or more wearable computing devices, one or more tablet computing devices, one or more desktop computing devices, one or more server computing devices, one or more combinations thereof, and the like. In one or more examples, the one or more computing devices 338 can cause at least a portion of the decoded digital data 334 to be output via one or more output devices, such as one or more speakers, one or more display devices, or a combination thereof. In one or more additional examples, the one or more computing devices 338 can cause at least a portion of the decoded digital data 334 to be accessible to one or more applications being executed by the one or more computing devices 338 or one or more applications being executed by one or more additional computing devices. In one or more further examples, the one or more computing devices 338 can cause at least a portion of the decoded digital data 334 to be stored in one or more data storage devices. For example, the one or more computing devices 338 can cause at least a portion of the decoded digital data 334 to be stored by one or more memory devices. In various examples, the one or more computing devices 338 can cause at least a portion of the decoded digital data 334 to be stored by one or more portable data storage devices.

Figure 4:
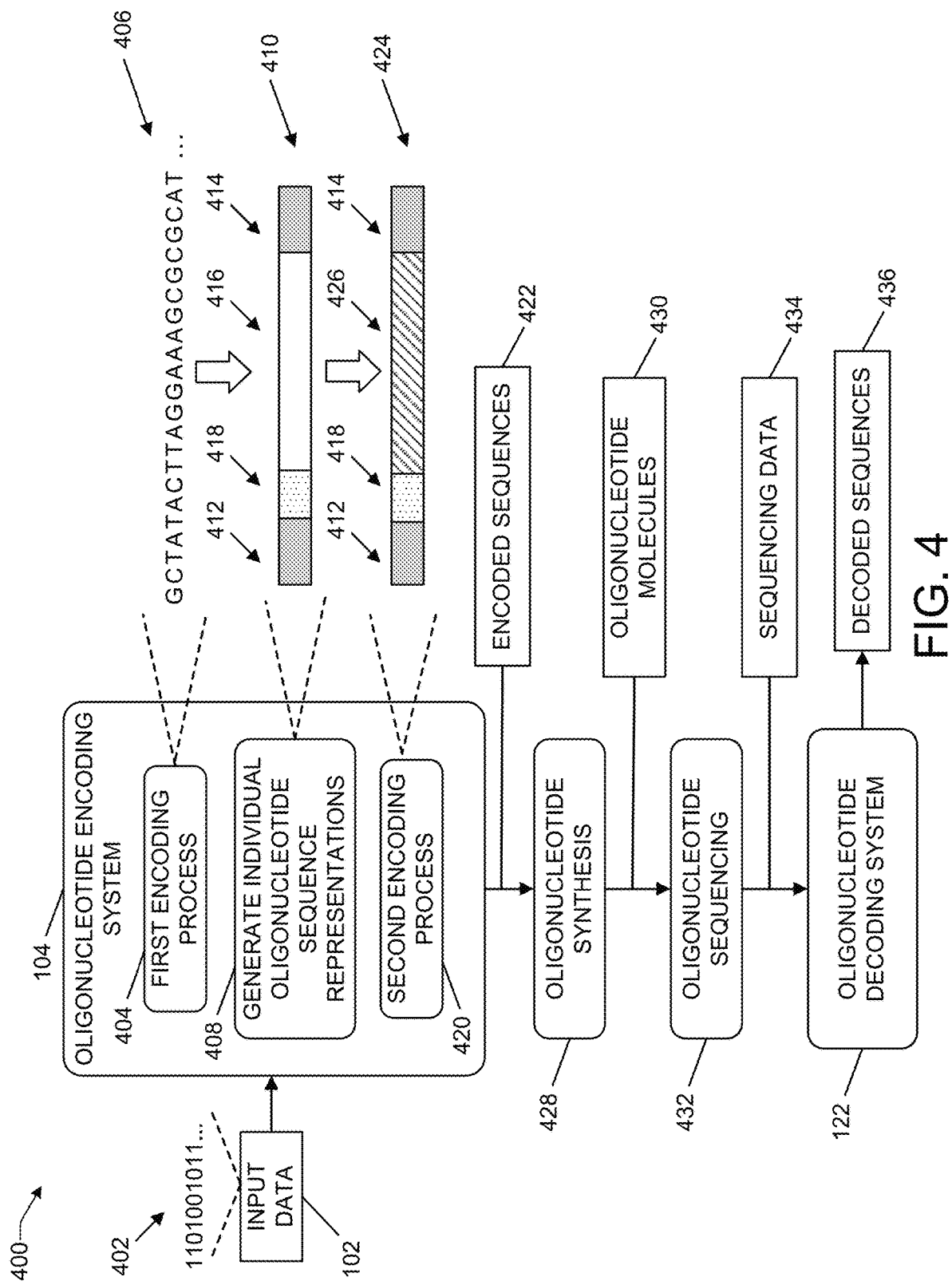
FIG. 4 is a diagram of a framework to encode digital data using oligonucleotides and decode the digital data stored by the oligonucleotides according to an encoding process that uses an encryption key included in the oligonucleotide sequences, in accordance with one or more implementations.

FIG. 4 is a diagram of a framework 400 to encode data using oligonucleotides and decode data stored by the oligonucleotides according to an encoding process that uses an encryption key included in oligonucleotide sequence representations, in accordance with one or more implementations. The framework 400 can include the oligonucleotide encoding system 104. The oligonucleotide encoding system 104 can analyze the input data 102. The input data 102 can include digital data that has been generated by one or more applications executed by one or more computing devices. In one or more examples, the input data 102 can be represented according to one or more positional number systems. In at least some examples, the input data 102 can include a first string of characters 402, such as a string of alphanumeric characters that represent the digital data. In one or more illustrative examples, input data 102 can be represented by a binary number system. In these scenarios, the input data 102 can include a number of bits and a number of bytes.

The oligonucleotide encoding system 104 can implement a first encoding process 404 to generate an encoded nucleotide sequence representation 406 from the from the first string of characters 402. In one or more examples, the first encoding process 404 can transform the input data 102 to a second string of characters with individual characters of the second string of characters being represented by nucleotides included in at least one of DNA or RNA. In this way, the first encoding process 404 can generate the encoded nucleotide sequence representation 406 to include a string of characters that includes one or more A's, one or more G's, one or more C's, one or more T's, and, in cases where the encoded nucleotide sequence representation 406 corresponds to RNA, one or more U's instead of one or more T's. The first encoding process 404 can include transforming combinations of characters included in the input data 102 to one or more characters included in DNA and/or RNA sequences to generate the encoded nucleotide representation 406 according to a first encoding scheme. In one or more illustrative examples, the oligonucleotide encoding system 104 can implement the first encoding process 404 to transform a 00 combination in the first string of characters 402 as an A in the encoded nucleotide sequence representation 406, a 01 combination in the first string of characters 402 as a T in the encoded nucleotide sequence representation 406, a 10 combination in the first string of characters 402 as a G in the encoded nucleotide sequence representation 406, and a 11 combination in the first string of characters 402 as a C in the encoded nucleotide sequence representation 406. Although an example first encoding scheme has been described above as an illustrative example, a number of different encoding schema can be implemented by the oligonucleotide encoding system 104 in the first encoding process 404 to generate the encoded oligonucleotide representation 406 from the input data 102.

The oligonucleotide encoding system 104 can also, at operation 408, generate a number of individual sequence representations based on the encoded nucleotide sequence representation 406. In one or more examples, the oligonucleotide encoding system 104 can divide the encoded nucleotide sequence representation 406 into a number of groups of characters with individual groups of characters corresponding to individual sequence representations. In various examples, the oligonucleotide encoding system 104 can generate tens of individual sequence representations from the encoded nucleotide sequence representation 406, hundreds of individual sequence representations from the encoded nucleotide sequence representation 406, thousands of individual sequence representations from the encoded nucleotide sequence representation 406, tens of thousands of individual sequence representations from the encoded nucleotide sequence representation 406, up to hundreds of thousands of individual sequence representations from the encoded nucleotide sequence representation 406, or more. In at least some examples, the individual sequence representations generated from the encoded nucleotide sequence representation 406 can include from about 50 nucleotides to about 500 nucleotides, from about 100 nucleotides to about 300 nucleotides, from about 200 nucleotides to about 400 nucleotides, from about 100 nucleotides to about 250 nucleotides, or from about 300 nucleotides to about 500 nucleotides.

In various examples, the oligonucleotide encoding system 104 can generate individual sequence representations that comprise segments that include a portion of the encoded nucleotide representation 406 and one or more additional segments. To illustrate, an example sequence representation 410 generated at operation 408 can include a first segment 412 that corresponds to a first primer and a second segment 414 that corresponds to a second primer. The first primer and the second primer can be used in one or more sequencing operations performed in relation to oligonucleotide molecules that have been synthesized based on the individual sequence representations generated by the oligonucleotide encoding system 104 at operation 408. The example sequence representation 410 can also include a third segment 416 that corresponds to a portion of the encoded nucleotide sequence representation 406. Additionally, the example sequence representation 410 can include a fourth segment 418 that corresponds to an encryption key. In at least some examples, the fourth segment 418 can indicate an order of the example sequence representation 410 in the encoded nucleotide sequence representation 406. In one or more examples, the oligonucleotide encoding system 104 can implement a second encoding process 420 that uses the encryption key included in the fourth segment 418 of the individual sequence representations to generate encoded sequences 422 that include a modified version of the third segment 416. In one or more illustrative examples, the second encoding process 420 can include implementing one or more encryption processes using the encryption keys to modify the nucleotides present at one or more positions of the third segment 416. To illustrate, the second encoding process 420 can produce encoded sequences 422 that correspond to modified versions of the example sequence representations 410. In the illustrative example of FIG. 4, a modified example sequence representation 424 can include the first segment 412, the second segment 414, a modified third segment 426, and the fourth segment 418. In various illustrative examples, the second encoding process 420 can include applying an XOR operation with a pseudo-random sequence generated using the encryption key in relation to the third segment 416.

The framework 400 can also include oligonucleotide synthesis 428 that causes oligonucleotide molecules 430 to be physically synthesized according to the encoded sequences 422 generated by the second encoding process 420. The oligonucleotide synthesis 428 can be performed in accordance with the oligonucleotide synthesizer apparatus 110 described in relation to FIG. 1.

In addition, oligonucleotide sequencing 432 can be performed using the oligonucleotide molecules 430. The oligonucleotide sequencing 432 can produce many copies of individual oligonucleotide molecules 430. For example, the oligonucleotide sequencing 432 can produce an amplification product that includes thousands, tens of thousands, up to millions of copies of individual oligonucleotide molecules 430. In one or more illustrative examples, the oligonucleotide sequencing 432 can include high-throughput sequencing operations. In one or more illustrative examples, the oligonucleotide sequencing 432 can be performed in accordance with at least one of the sequencing apparatus 118 described in relation to FIG. 1 or the sequencing operations 304 described in relation to FIG. 3.

The oligonucleotide sequencing 432 can generate sequencing data 434. The sequencing data 434 can include alphanumeric sequence representations of the oligonucleotide molecules 430 included in an amplification product produced by the oligonucleotide sequencing 432. For example, the sequencing data 434 can include, for individual oligonucleotide molecules included in the amplification product, data that corresponds to a string of characters that represent the respective chains of nucleotides that correspond to the individual oligonucleotide molecules of the amplification product. In at least some examples, the sequencing data 434 can include sequencing reads. In one or more examples, the sequencing data 434 can be stored in one or more data files.

The framework 400 can also include the oligonucleotide decoding system 122. The oligonucleotide decoding system 122 can analyze the sequencing data 434 to generate decoded sequences 436. In one or more examples, the oligonucleotide decoding system 122 can determine a segment of the individual sequencing reads included in the sequencing data 434 that correspond to the encryption keys for the oligonucleotide molecules 430. In one or more illustrative examples, the segments that correspond to the encryption keys can be located at one or more positions of the oligonucleotide molecules 430. In one or more additional illustrative examples, the segments that correspond to the encryption keys are located at a same set of positions of the oligonucleotide molecules 430. After identifying the encryption keys included in the sequencing reads of the sequencing data 434, the oligonucleotide decoding system 122 can determine the segment of the sequencing reads that correspond to the payload. For individual sequencing reads, the oligonucleotide decoding system 122 can implement one or more decryption techniques with respect to the payload that correspond to the encryption techniques used to generate the payload. In this way, the oligonucleotide decoding system 122 can determine the decoded sequences 436 based on decrypted payloads of the sequencing reads included in the sequencing data 434.

In at least some examples, the oligonucleotide decoding system 122 can analyze the sequencing data 434 to determine consensus nucleotide sequences that correspond to a number of sequencing reads that originate from a same oligonucleotide molecule 430. In one or more examples, the oligonucleotide decoding system 122 can determine the segments corresponding to the respective encryption keys and the respective payloads of the consensus nucleotide sequences. The oligonucleotide decoding system 122 can then decrypt the payloads of the consensus nucleotide sequences using the encryption keys to produce the decoded sequences 436.

In various examples, after producing the decoded sequences 436, the oligonucleotide decoding system 122 can implement a second decoding process to generate a string of characters that corresponds to the digital data that is to be retrieved. In one or more examples, the second decoding process can implement at least one of one or more rules or one or more schemes that correspond to the first encoding process 404 that was used to generate the encoded nucleotide sequence representation 406. In at least some examples, the decoded digital data can be accessed by one or more computing devices.

Figure 5:
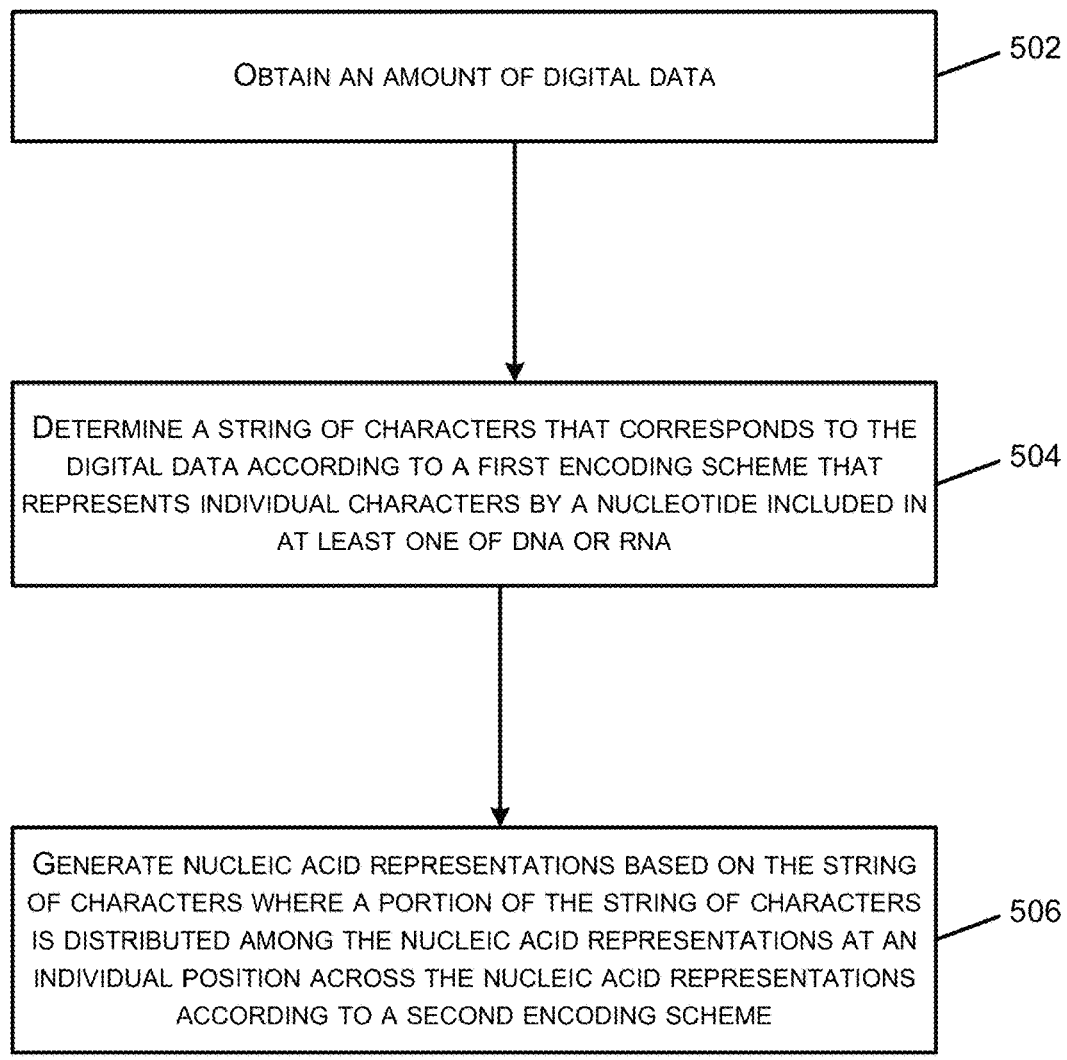
FIG. 5 is a flow diagram of an example process to encode digital data using oligonucleotides according to multiple encoding schemes, in accordance with one or more implementations.
Figure 6:
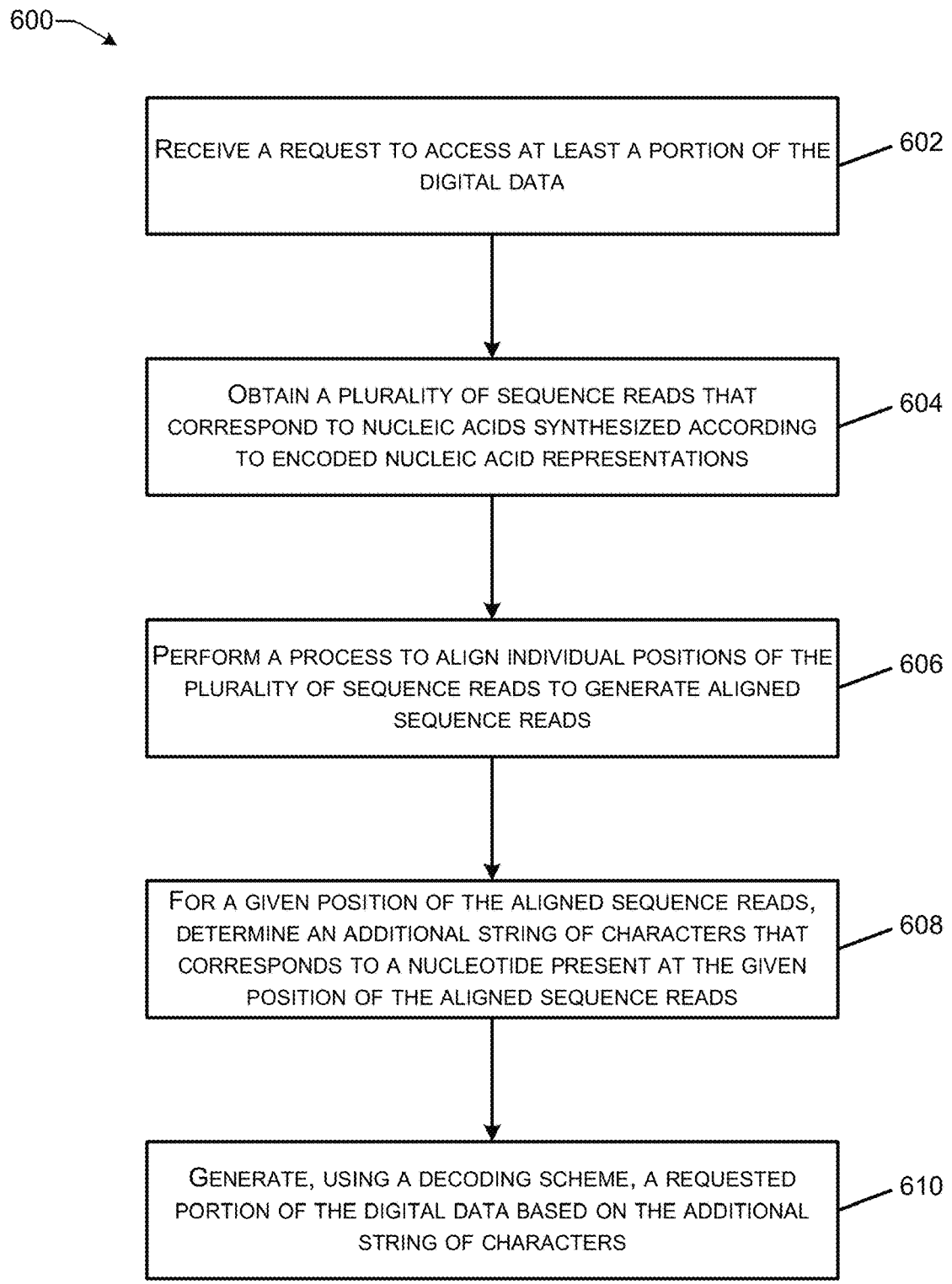
FIG. 6 is a flow diagram of an example process to decode digital data that has been encoded using oligonucleotides according to multiple encoding processes, in accordance with one or more implementations.
Figure 7:
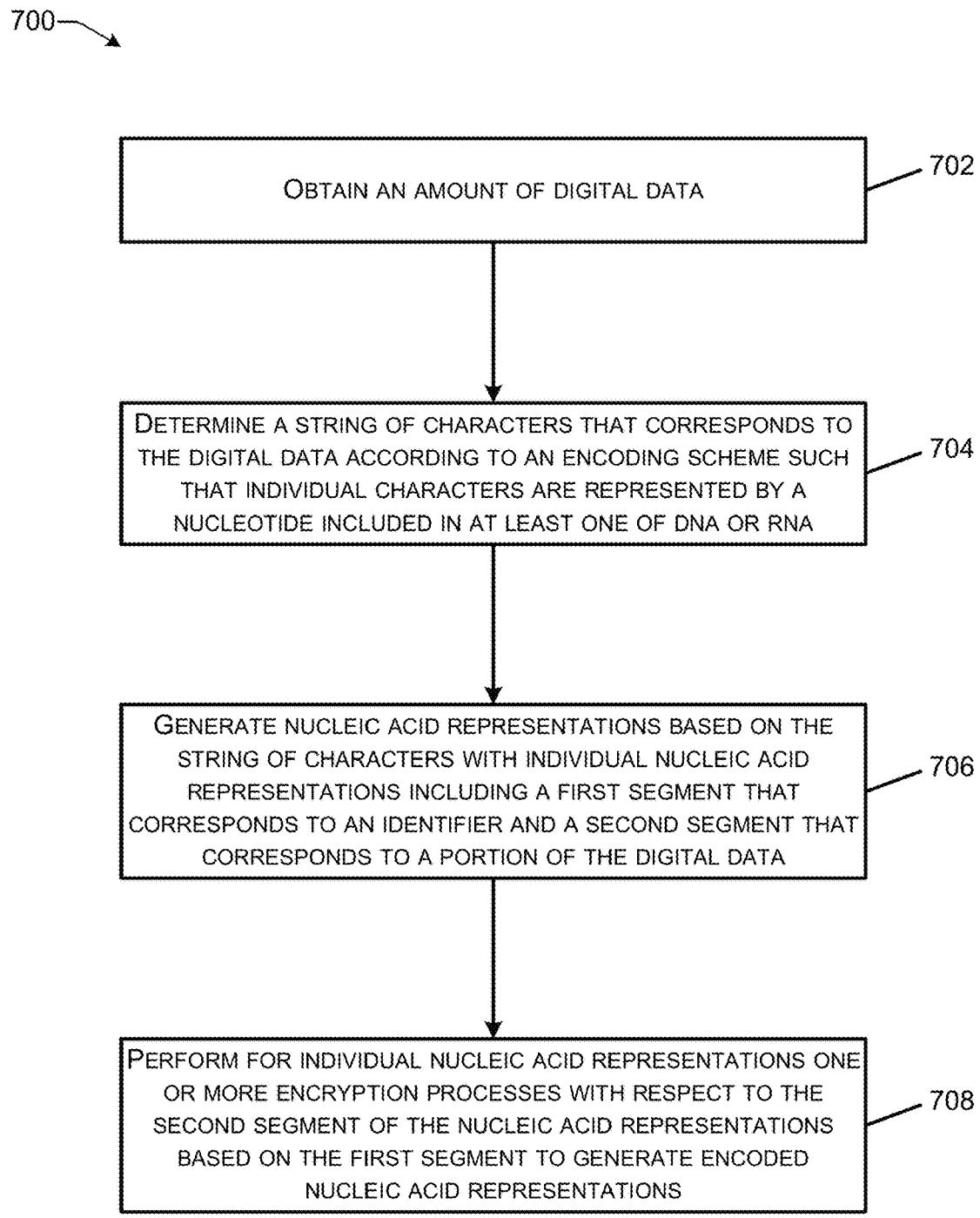
FIG. 7 is a flow diagram of an example process to encode digital data using oligonucleotides and decode the digital data stored by the oligonucleotides according to an encoding process that uses an encryption key included in the oligonucleotide sequence representations, in accordance with one or more implementations.

FIG. 5, FIG. 6, and FIG. 7 illustrate example processes for encoding and decoding digital data using oligonucleotides. The example processes are illustrated as collections of blocks in logical flow graphs, which represent sequences of operations that can be implemented in hardware, software, or a combination thereof. The blocks are referenced by numbers. In the context of software, the blocks represent computer-executable instructions stored on one or more computer-readable media that, when executed by one or more processing units (such as hardware microprocessors), perform the recited operations. Generally, computer-executable instructions include routines, programs, objects, components, data structures, and the like that perform particular functions or implement particular data types. The order in which the operations are described is not intended to be construed as a limitation, and any number of the described blocks can be combined in any order and/or in parallel to implement the process.

FIG. 5 is a flow diagram of an example process 500 to encode data using oligonucleotides according to multiple encoding schemes, in accordance with one or more implementations. The process 500 can include, at operation 502, obtaining an amount of digital data. The digital data can be generated by one or more computing devices and be represented by a positional number system. In one or more examples, the digital data can be stored in a plurality of data files.

In addition, at operation 504, the process 500 can include determining a string of characters that correspond to the digital data. The string of characters can be determined according to a first encoding scheme or technique that represents individual characters by a nucleotide included in at least one of DNA or RNA. In one or more examples, string of characters can include a number of 0s and a number of 1s when the digital data is represented by a binary number system. In various examples, a number of combinations of 0s and 1s can be represented by one or more characters that represent nucleotides included in at least one of DNA or RNA, such as A, T, G, C, and/or U.

Further, the process 500 can include, at operation 506, generating nucleic acid representations based on the string of characters. In at least some examples, the nucleic acid representations can be generated based on a second encoding scheme or technique. A portion of the string of characters can be distributed among the nucleic acid representations at an individual position across the nucleic acid representations. In one or more examples, the string of characters can be divided into a number of groups of characters. Individual groups of characters can correspond to individual nucleic acid representations. In various examples, the nucleic acid representations can be used to synthesize nucleic acid molecules and then stored for later retrieval when at least a portion of the amount of digital data is to be retrieved.

The encoding techniques or schemes used to generate the string of characters and the nucleic acid representations can produce a group of nucleic acid representations such that undesirable patterns within the nucleic acid representations are minimized. For example, the encoding techniques or schemes used to generate at least one of the string of characters or the nucleic acid representations can produce nucleic acid representations comprising one or more segments having no greater than a threshold frequency of a given pattern of one or more nucleotides. In one or more illustrative examples, the threshold frequency of the given pattern can include no more than 2 instances of the given pattern within a segment of the nucleic acid representations, no more than 3 consecutive instances of the given pattern within a segment of the nucleic acid representations, no more than 4 consecutive instances of the given pattern within a segment of the nucleic acid representations, no more than 5 consecutive instances of the given pattern within a segment of the nucleic acid representations, no more than 6 consecutive instances of the given pattern within a segment of the nucleic acid representations, no more than 7 consecutive instances of the given pattern within a segment of the nucleic acid representations, no more than 8 consecutive instances of the given pattern within a segment of the nucleic acid representations, no more than 9 consecutive instances of the given pattern within a segment of the nucleic acid representations, or no more than 10 consecutive instances of the given pattern within a segment of the nucleic acid representations.

In one or more examples, the given pattern can include a repetition of a single nucleotide, pair of nucleotides in the nucleic acid representations. In one or more additional examples, the given pattern can include a repetition of a pair of nucleotides in the nucleic acid representations. In one or more further examples, the given pattern can include a repetition of a trimer of nucleotides in the nucleic acid representations. In various examples, the segment of the nucleic acid representations in which the given pattern is present can include no greater than 5 nucleotides, no greater than 8 nucleotides, no greater than 10 nucleotides, no greater than 12 nucleotides, no greater than 15 nucleotides, no greater than 18 nucleotides, no greater than 20 nucleotides, no greater than 25 nucleotides, or no greater than 30 nucleotides. In still other examples, nucleotides of the individual nucleic acid representations are ordered such that a probability of at least two nucleotides interacting to form a hairpin structure in nucleic acid molecules generated based on the individual nucleic acid representations is less than a threshold probability. In at least some examples, the threshold probability can be no greater than 30%, no greater than 25%, no greater than 20%, no greater than 15%, no greater than 10%, no greater than 5%, no greater than 3%, or no greater than 1%.

In various examples, the second encoding scheme can be linear and the string of characters can be distributed among the nucleic acid representations according to a transverse arrangement such that a first portion of the string of characters is distributed at a first position of each of the nucleic acid representations and a second portion of the string of characters is distributed at a second position of each of the nucleic acid representations. In one or more additional examples, the second encoding scheme can be non-linear. In these scenarios, the portion of the string of characters can be distributed across positions of the individual nucleic acid representations such that a first character of the string of characters is represented at a first position of a first nucleic acid representation and is offset by one or more positions with respect to a second character of the string of characters that is represented at a second position of a second nucleic acid representation. The first character and the second character can be consecutive characters in the string of characters and the first nucleic acid representation and the second nucleic acid representation can be ordered consecutively within the string of characters.

In at least some examples, multiple encoding techniques can be combined to generate the nucleic acid representations. For example, in addition to using a transverse encoding scheme that identifies nucleotides to include in the nucleic acid representations according to a given pattern, the nucleic acid representations can also be generated by applying one or more encryption techniques. In one or more examples, the one or more encryption techniques can be applied before the transverse encoding scheme is implemented. In one or more additional examples, the one or more encryption techniques can be implemented after the transverse encoding scheme is implemented. In various examples, the one or more encryption techniques can be applied according to an encryption key. The encryption key can include one or more nucleotides present in the nucleic acid representations that identify the respective nucleic acid representations. In one or more illustrative examples, the one of more nucleotides that identify the nucleic acid representations can uniquely identify individual nucleic acid representations. In one or more scenarios, the one or more nucleotides that identify the respective nucleic acid representations can indicate an order of individual nucleic acid representations with respect to the encoded nucleotide sequence representation that is comprised of the string of characters.

FIG. 6 is a flow diagram of an example process 600 to decode data that has been encoded using oligonucleotides according to multiple encoding processes, in accordance with one or more implementations. The process 600 can include, at operation 602, receiving a request to access at least a portion of digital data that has been encoded using oligonucleotides. At operation 604, the process 600 can include obtaining a plurality of sequencing reads that correspond to nucleic acids synthesized according to encoded nucleic acid representations. In one or more examples, individual sequencing reads of the plurality of sequences reads can include a first segment indicating a primer used in a sequencing process that generates the plurality of sequencing reads. Additionally, individual sequencing reads of the plurality of sequences reads can include a second segment can indicate a location of the individual sequencing read with respect to an order in which the plurality of sequencing reads are to be aligned. Further, individual sequencing reads of the plurality of sequences reads can include a third segment indicating a payload that corresponds to a number of nucleotides that encode a portion of the digital data. In various examples, for a first position of the aligned sequencing reads, a nucleotide present at the first position of each of the aligned sequencing reads can be determined to generate a first portion of the additional string of characters. In one or more additional examples, for a second position of the aligned sequencing reads, an additional nucleotide present at the second position of each of the aligned sequencing reads can be determined to generate a second portion of the additional string of characters.

In addition, the process 600 can include, at operation 606, performing a process to align individual positions of the plurality of sequencing reads to generate aligned sequencing reads. In one or more examples, prior to aligning the plurality of sequencing reads, the plurality of sequencing reads can be analyzed to determine a number of clusters of sequencing reads. Individual clusters of the plurality of sequencing reads can correspond to one or more copies of a given nucleic acid that was subject to one or more sequencing operations. In various examples, a plurality of consensus sequencing reads can be determined that individually correspond to an individual cluster of sequencing reads. In one or more additional examples, the plurality of consensus sequencing reads can be aligned. In one or more illustrative examples, the number of clusters of sequencing reads can be determined by determining a measure of similarity between a first nucleotide sequence of one or more first sequencing reads included the plurality of sequencing reads and a second nucleotide sequence of one or more second sequencing reads included in the plurality of sequencing reads. In scenarios where the measure of similarity is at least a threshold measure of similarity, the first nucleotide sequences and the second nucleotide sequences can be associated with a same consensus sequence.

Further, at operation 608, the process 600 can include, for a given position of the aligned sequencing reads, determining an additional string of characters that corresponds to a nucleotide present at the given position of the aligned sequencing reads. That is, the additional string of characters can be comprised of nucleotides generated by selecting nucleotides according to a pattern of positions of the aligned sequencing reads. The additional string of characters can include individual characters that correspond to letters that are related to nucleotides present in at least one of DNA or RNA. The process 600 can also include, at operation 610, generating, using a decoding scheme, a requested portion of the digital data based on the additional string of characters. For example, one or more characters in the additional string of characters can be translated from A's, G's, T's, C's, and/or U's to 1's and 0's according to the decoding scheme.

FIG. 7 is a flow diagram of an example process 700 to encode data using oligonucleotides and decode data stored by the oligonucleotides according to an encoding process that uses an encryption key included in the oligonucleotide sequences, in accordance with one or more implementations. The process 700 can include, at operation 702, obtaining an amount of digital data. Additionally, at operation 704, the process 700 can include determining a string of characters that corresponds to the digital data according to an encoding scheme such that individual characters are represented by a nucleotide included in at least one DNA or RNA.

At operation 706, the process 700 can also include generating nucleic acid representations based on the string of characters with individual nucleic acid representations including a first segment that corresponds to an identifier and a second segment that corresponds to a portion of the digital data. Further, the process 700 can include, at operation 708, performing for individual nucleic acid representations one or more encryption processes with respect to the second segment of the nucleic acid representations based on the first segment to generate encoded nucleic acid representations. In one or more illustrative examples, the one or more encryption processes can include an XOR randomization process.

In one or more examples, the encrypted nucleic acid representations can be subjected to one or more decryption processes in response to a request to access one or more portions of the digital data. In at least some examples, oligonucleotide molecules can be synthesized that correspond to the nucleic acid representations and the oligonucleotide molecules can be stored in a storage container. Responsive to a request to a access at least a portion of the digital data, one or more sequencing operations can be performed to produce an amplification product that includes a plurality of oligonucleotide molecules that correspond to individual nucleic acid representations. Sequencing data can be generated that includes a plurality of sequencing reads that correspond to the plurality of oligonucleotide molecules included in the amplification product. In various examples, the sequencing data can be analyzed according to one or more decoding schemes to generate an additional string of characters that corresponds to the amount of digital data that for which access is requested. For example, the plurality of sequencing reads can be analyzed to determine one or more sequencing reads of the plurality of sequencing reads that correspond to a given nucleic acid representation of the plurality of nucleic acid representations. In one or more illustrative examples, the plurality of sequencing reads can correspond to a consensus sequence. Further, the decoding scheme can include, for a given position of the one or more sequencing reads, determining an additional string of characters based on nucleotides present at individual positions of the one or more sequencing reads. The additional string of characters can correspond to the requested amount of digital data and can be accessible to one or more computing devices.

Figure 8:
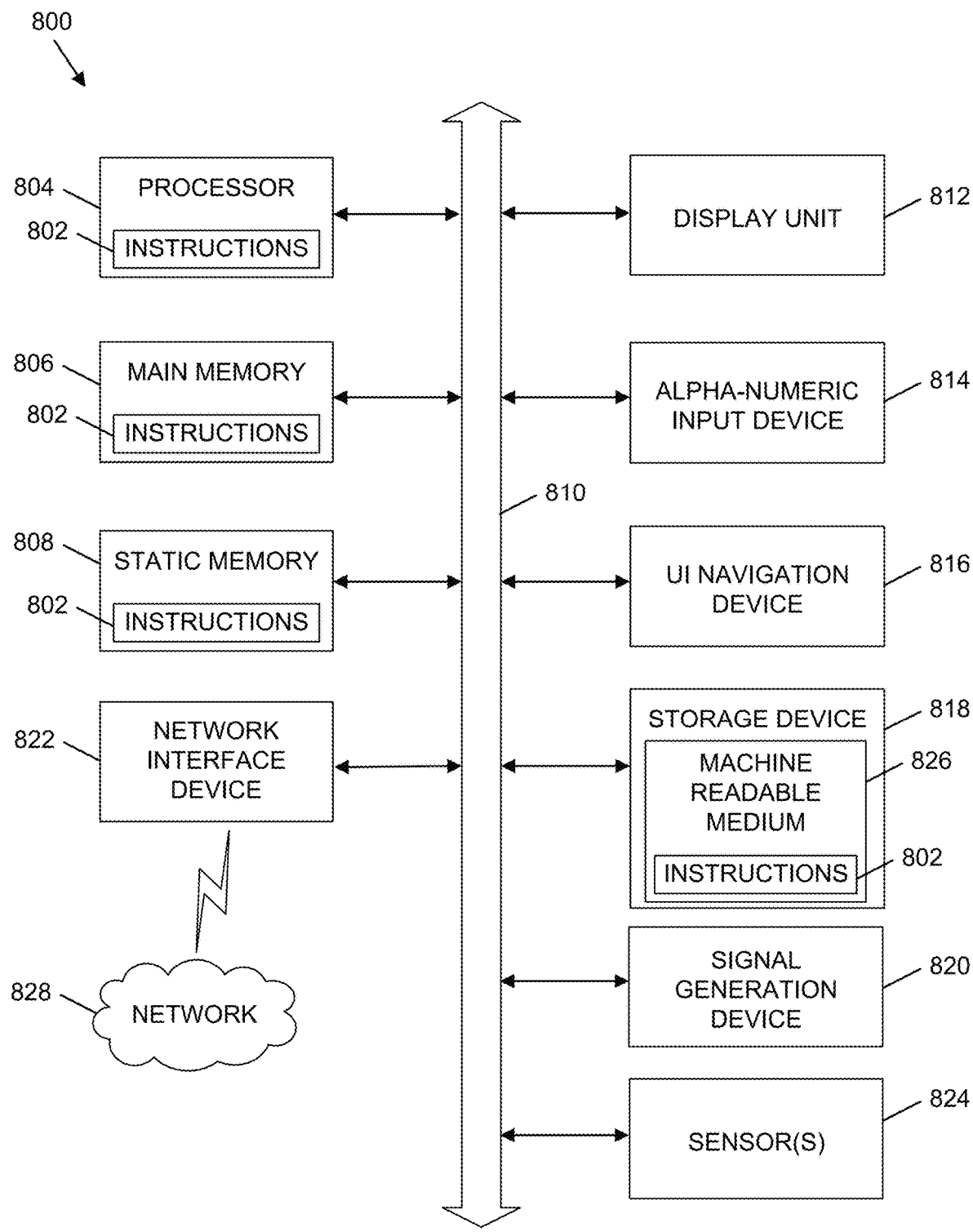
FIG. 8 illustrates a diagrammatic representation of a machine in the form of a computer system within which a set of instructions may be executed for causing the machine to perform any one or more of the methodologies discussed herein, according to an example embodiment.

FIG. 8 illustrates a diagrammatic representation of a machine 800 in the form of a computer system within which a set of instructions may be executed for causing the machine 800 to perform any one or more of the methodologies discussed herein, according to an example, according to an example embodiment. Specifically, FIG. 8 shows a diagrammatic representation of the machine 800 in the example form of a computer system, within which Instructions 802 (e.g., software, a program, an application, an applet, an app, or other executable code) for causing the machine 800 to perform any one or more of the methodologies discussed herein may be executed. For example, the Instructions 802 may cause the machine 800 to implement the frameworks and architectures 100, 200, 300, 400, described with respect to FIGS. 1, 2, 3, and 4, respectively, and to execute the methods 500, 600, 700 described with respect to FIGS. 5, 6, and 7, respectively.

The Instructions 802 transform the general, non-programmed machine 800 into a particular machine 800 programmed to carry out the described and illustrated functions in the manner described. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the Instructions 802, sequentially or otherwise, that specify actions to be taken by the machine 800. Further, while only a single machine 800 is illustrated, the term "machine" shall also be taken to include a collection of machines 800 that individually or jointly execute the Instructions 802 to perform any one or more of the methodologies discussed herein.

Examples of computing device 800 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine-readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., computing device 800) and software architectures that can be deployed in example embodiments.

In an example, the computing device 800 can operate as a standalone device or the computing device 800 can be connected (e.g., networked) to other machines.

In a networked deployment, the computing device 800 can operate in the capacity of either a server or a client machine in server-client network environments. In an example, computing device 800 can act as a peer machine in peer-to-peer (or other distributed) network environments. The computing device 800 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the computing device 800. Further, while only a single computing device 800 is illustrated, the term "computing device" shall also be taken to include any collection of machines that individually or jointly execute a set (or multiple sets) of instructions to perform any one or more of the methodologies discussed herein.

Example computing device 800 can include a processor 804 (e.g., a central processing unit CPU), a graphics processing unit (GPU) or both), a main memory 806 and a static memory 808, some or all of which can communicate with each other via a bus 810. The computing device 800 can further include a display unit 812, an alphanumeric input device 814 (e.g., a keyboard), and a user interface (UI) navigation device 816 (e.g., a mouse). In an example, the display unit 812, input device 814 and UI navigation device 816 can be a touch screen display. The computing device 800 can additionally include a storage device (e.g., drive unit) 818, a signal generation device 820 (e.g., a speaker), a network interface device 822, and one or more sensors 824, such as a global positioning system (GPS) sensor, compass, accelerometer, or another sensor.

The storage device 818 can include a machine readable medium 826 on which is stored one or more sets of data structures or Instructions 802 (e.g., software) embodying or utilized by any one or more of the methodologies or functions described herein. The Instructions 802 can also reside, completely or at least partially, within the main memory 806, within static memory 808, or within the processor 804 during execution thereof by the computing device 800. In an example, one or any combination of the processor 804, the main memory 806, the static memory 808, or the storage device 818 can constitute machine readable media.

While the machine readable medium 826 is illustrated as a single medium, the term "machine readable medium" can include a single medium or multiple media (e.g., a centralized or distributed database, and/or associated caches and servers) that configured to store the one or more Instructions 802. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine-readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 802 can further be transmitted or received over a communications network 828 using a transmission medium via the network interface device 822 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Examples

Various aspects of the present invention can be better understood by reference to the following Examples which are offered by way of illustration. The inventive concepts described in the application are not limited to the Examples given herein.

Figure 9:
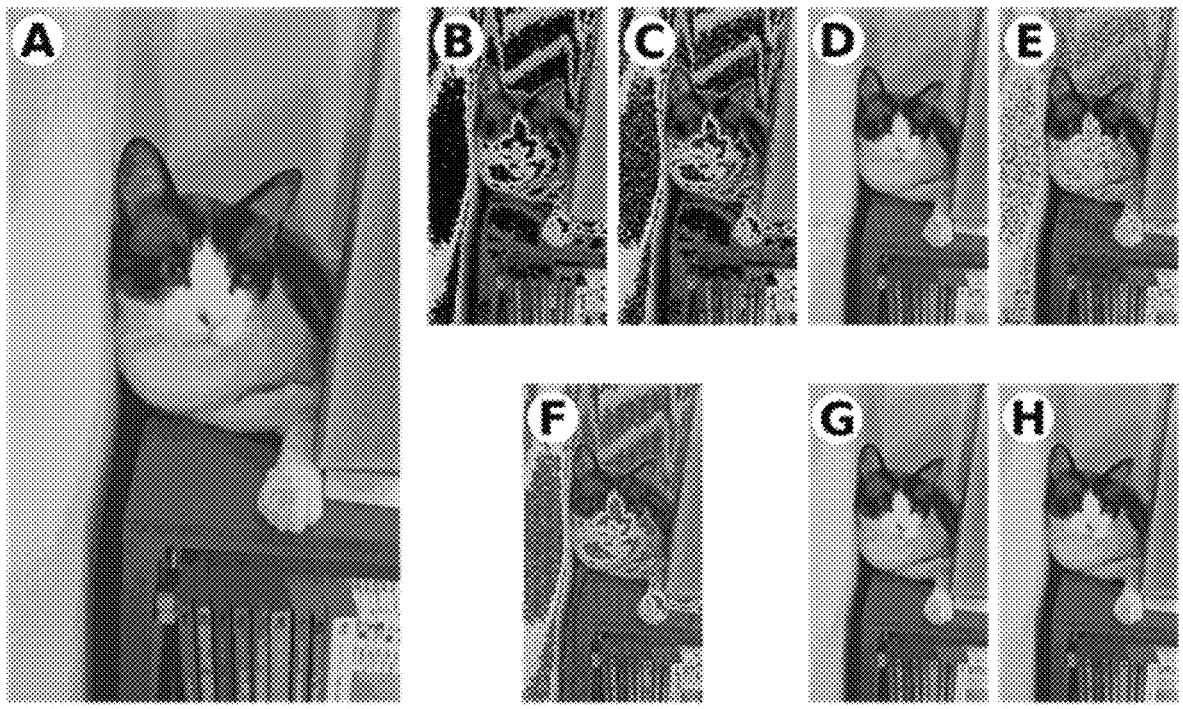
FIG. 9 illustrates reproductions of an image that was encoded and decoded according to various encoding and decoding processes.

We illustrate the performance of the claimed methods by comparing them with literature methods. For all tests, we encode the same 720×1280 bitmap image (2.63 MB) into nucleotide sequences. A bitmap image is used to allow visual inspection of file retrievability. The original image is shown in FIG. 9, item A. In the tests, each sequence has 19 nucleotide (nt) primers in both ends and an address of size 16 nt. One substitution error can be corrected in each sequence with Reed-Solomon Code, and no outer code is used (missing sequences cannot be recovered). The exact size of the sequences varies according to each coding scheme, but they are all in the range from 150 nt to 200 nt. We simulated random errors in the sequences in silico, including multiple reads for the same sequence. For clustering and aligning the reads after sequencing, we use Cutadapt v4.2 and Vsearch v2.22.1 (bioinformatic tools).

FIG. 9, item B; FIG. 9, item C; and FIG. 9, item D show the image retrieved with literature methods, namely, the ones proposed by Goldman (rotating mapping scheme only), Blawat (mapping scheme only), and Grass (but without outer code). The black and wrongly colored regions in the images are the parts of the file that has failed to be retrieved. Comment overall aspect, black areas. The byte error rates (BER) of the retrieved images are shown in the second column in Table 1. With Goldman and Blawat's methods, the error rate is remarkably high (around 30%). With the Grass method, the error rate is lower, around 1%, and the improvement is probably because of the block transversal arrangement.

FIG. 9, item E shows the image retrieved using YinYang Codec. This method has improved performance, with a 6% of error rate, because the technique randomly mixes two binary segments to generate each nucleotide sequence.

FIG. 9, item F shows the image retrieved with the Blawat method, now also using global randomization as found in Organick et al., 2018 (by applying the XOR operation of the binary data of the file with a pre-defined random kernel of size 48 bits, repeated along the file data). Note that this approach needs to improve the retrieval quality compared to the Blawat method alone.

The claimed methods are evaluated along with the Blawat encoding scheme. FIG. 9, item G shows the image retrieved using Blawat with address randomization (applying XOR with a distinct random data segment for each sequence). FIG. 9, item H shows the image retrieved using Blawat with global transversal data arrangement. Note that the proposed methods improve the robustness of the decoding, decreasing the error rate to below 0.01%.

We also encoded the image with these seven coding methods now including outer code to retrieve missing sequences. We used Reed-Solomon code inserting 12 redundant sequences every 200 data sequences, which makes it possible to retrieve 12 missing sequence every 212 sequences (error-correcting capacity of 5.6%). The byte error rate of these methods with outer code is shown in the third column of Table 1. Note that the coding schemes that have resulted in error rates below the outer code error-correcting capacity, which includes the claimed methods, had integral retrieval with outer code.

TABLE 1

| Coding Scheme | BER (no OC) | BER (with OC) |
| --- | --- | --- |
| (B) Goldman mapping | 0.33029 | 0.32755 |
| (C) Blawat mapping | 0.29450 | 0.29375 |
| (D) Grass coding scheme | 0.01028 | 0.0 |
| (E) YinYang CODEC | 0.0686 | 0.04239 |
| (F) Blawat (global rand.) | 0.3314 | 0.32962 |
| (G) Blawat (address rand.) [proposal] | 0.000017 | 0.0 |
| (H) Blawat (transversal) [proposal] | 0.000098 | 0.0 |

EXAMPLE ASPECTS OF THE DISCLOSURE

The following exemplary aspects are provided, the numbering of which is not to be construed as designating levels of importance:

Aspect 1. A system comprising: one or more processors; and memory storing computer-readable instructions that, when executed by the one or more processors, cause the one or more processors to perform operations comprising: obtaining an amount of digital data stored in one or more data files; determining a string of characters that corresponds to the digital data according to a first encoding scheme such that individual characters of the string of characters are represented by a nucleotide included in at least one of deoxyribonucleic acid (DNA) or ribonucleic acid (RNA); generating nucleic acid representations based on the string of characters, wherein individual nucleic acid representations include a plurality of positions and a portion of the string of characters is distributed among the nucleic acid representations at an individual position across the nucleic acid representations according to a second encoding scheme; receiving a request to access at least a portion of the digital data; obtaining a plurality of sequencing reads that correspond to nucleic acids synthesized according to the nucleic acid representations, wherein the plurality of sequencing reads indicate nucleotides present at individual positions of the nucleic acids; performing a process to align individual positions of the plurality of sequencing reads to generate aligned sequencing reads; for a given position of the aligned sequencing reads, determining an additional string of characters that corresponds to a nucleotide present at the given position of the aligned sequencing reads; and generating, using a decoding scheme, a requested portion of the digital data based on the additional string of characters.

Aspect 2. The system of aspect 1, wherein the nucleic acid representations comprise segments having no greater than a threshold frequency of a given pattern of one or more nucleotides.

Aspect 3. The system of aspect 2, wherein the given pattern is repetition of a pair of nucleotides at a threshold number of consecutive pairs of positions of the nucleic acid representations.

Aspect 4. The system of aspect 2, wherein the given pattern is repetition of a set of three nucleotides at a threshold number of consecutive positions of the nucleic acid representations.

Aspect 5. The system of any one of aspects 1-4, wherein individual sequencing reads of the plurality of sequences reads include: a first segment indicating a primer used in a sequencing process that generates the plurality of sequencing reads; a second segment indicating a location of the individual sequencing read with respect to an order in which the plurality of sequencing reads are to be aligned; and a third segment indicating a payload that corresponds to a number of nucleotides that encode a portion of the digital data.

Aspect 6. The system of any one of aspects 1-5, wherein the memory stores additional computer-readable instructions that, when executed by the one or more processors, cause the one or more processors to perform additional operations comprising: for a first position of the aligned sequencing reads, determining a nucleotide present at the first position of each of the aligned sequencing reads to generate a first portion of the additional string of characters; and for a second position of the aligned sequencing reads, determining an additional nucleotide present at the second position of each of the aligned sequencing reads to generate a second portion of the additional string of characters.

Aspect 7. The system of any one of aspects 1-6, wherein the memory stores additional computer-readable instructions that, when executed by the one or more processors, cause the one or more processors to perform additional operations comprising: obtaining a collection of sequencing reads that correspond to nucleic acids synthesized according to the nucleic acid representations; analyzing the collection of sequencing reads to determine a number of clusters of sequencing reads, wherein individual clusters of the number of sequencing reads correspond to one or more copies of a given nucleic acid that was subject to one or more sequencing operations; and determining a plurality of consensus sequencing reads that individually correspond to an individual cluster of sequencing reads; wherein the plurality of sequencing reads includes the plurality of consensus sequencing reads.

Aspect 8. The system of aspect 7, wherein the memory stores additional computer-readable instructions that, when executed by the one or more processors, cause the one or more processors to analyze the collection of sequencing reads to determine the number of clusters of sequencing reads by: determining a measure of similarity between a first nucleotide sequence of one or more first sequencing reads included the collection of sequencing reads and a second nucleotide sequence of one or more second sequencing reads included in the collection of sequencing reads; determining that the measure of similarity is at least a threshold measure of similarity; and determining that the first nucleotide sequences and the second nucleotide sequences correspond to a same consensus sequence.

Aspect 9. The system of any one of aspects 1-8, wherein nucleotides of the individual nucleic acid representations are ordered such that a probability of the at least two nucleotides interacting to form a hairpin structure in nucleic acids corresponding to the individual nucleic acid representations is less than a threshold probability.

Aspect 10. The system of any one of aspects 1-9, wherein the memory stores additional computer-readable instructions that, when executed by the one or more processors, cause the one or more processors to generate nucleic acid representations based on the string of characters by: generating, for individual nucleic acid representations, a first segment that corresponds to an identifier of the individual nucleic acid representation and a second segment that corresponds to a portion of the digital data; and performing, for the individual nucleic acid representations, one or more encryption processes with respect to the second segment of the individual nucleic acid representations based on the first segment of the individual nucleic acid representations to generate a plurality of encoded nucleic acid representations.

Aspect 11. The system of aspect 10, wherein the one or more encryption processes include an XOR randomization process Aspect 12. The system of any one of aspects 1-11, wherein the second encoding scheme is linear and the string of characters is distributed among the nucleic acid representations according to a transverse arrangement such that a first portion of the string of characters is distributed at a first position of each of the nucleic acid representations and a second portion of the string of characters is distributed at a second position of each of the nucleic acid representations.

Aspect 13. The system of any one of aspects 1-12, wherein the second encoding scheme is non-linear and the portion of the string of characters is distributed across positions of the individual nucleic acid representations such that a first character of the string of characters is represented at a first position of a first nucleic acid representation and is offset by one or more positions with respect to a second character of the string of characters that is represented at a second position of a second nucleic acid representation, wherein the first character and the second character are consecutive characters in the string of characters and the first nucleic acid representation and the second nucleic acid representation are ordered consecutively.

Aspect 14. A method comprising: obtaining, by one or more computing devices including one or more processors and memory, an amount of digital data stored in one or more data files; determining, by the one or more computing devices, a string of characters that corresponds to the digital data according to a first encoding scheme such that individual characters of the string of characters are represented by a nucleotide included in at least one of deoxyribonucleic acid (DNA) or ribonucleic acid (RNA); generating, by the one or more computing devices, nucleic acid representations based on the string of characters, wherein individual nucleic acid representations include a plurality of positions and a portion of the string of characters is distributed among the nucleic acid representations at an individual position across the nucleic acid representations according to a second encoding scheme; receiving, by the one or more computing devices, a request to access at least a portion of the digital data; obtaining a plurality of sequencing reads that correspond to nucleic acids synthesized according to the nucleic acid representations, wherein the plurality of sequencing reads indicate nucleotides present at individual positions of the nucleic acids; performing, by the one or more computing devices, a process to align individual positions of the plurality of sequencing reads to generate aligned sequencing reads; for a given position of the aligned sequencing reads, determining, by the one or more computing devices, an additional string of characters that corresponds to a nucleotide present at the given position of the aligned sequencing reads; and generating, by the one or more computing devices and using a decoding scheme, a requested portion of the digital data based on the additional string of characters.

Aspect 15. The method of aspect 14, wherein the nucleic acid representations comprise segments having no greater than a threshold frequency of a given pattern of one or more nucleotides.

Aspect 16. The method of aspect 15, wherein the given pattern is repetition of a pair of nucleotides at a threshold number of consecutive pairs of positions of the nucleic acid representations.

Aspect 17. The method of aspect 15, wherein the given pattern is repetition of a set of three nucleotides at a threshold number of consecutive positions of the nucleic acid representations.

Aspect 18. The method of any one of aspects 14-17, wherein individual sequencing reads of the plurality of sequences reads include: a first segment indicating a primer used in a sequencing process that generates the plurality of sequencing reads; a second segment indicating a location of the individual sequencing read with respect to an order in which the plurality of sequencing reads are to be aligned; and a third segment indicating a payload that corresponds to a number of nucleotides that encode a portion of the digital data.

Aspect 19. The method of any one of aspects 14-18, comprising: for a first position of the aligned sequencing reads, determining, by the one or more computing devices, a nucleotide present at the first position of each of the aligned sequencing reads to generate a first portion of the additional string of characters; and for a second position of the aligned sequencing reads, determining, by the one or more computing devices, an additional nucleotide present at the second position of each of the aligned sequencing reads to generate a second portion of the additional string of characters.

Aspect 20. The method of any one of aspects 14-19, comprising: obtaining, by the one or more computing devices, a collection of sequencing reads that correspond to nucleic acids synthesized according to the nucleic acid representations; analyzing, by the one or more computing devices, the collection of sequencing reads to determine a number of clusters of sequencing reads, wherein individual clusters of the number of sequencing reads correspond to one or more copies of a given nucleic acid that was subject to one or more sequencing operations; and determining, by the one or more computing devices, a plurality of consensus sequencing reads that individually correspond to an individual cluster of sequencing reads; wherein the plurality of sequencing reads includes the plurality of consensus sequencing reads.

Aspect 21. The method of aspect 20, wherein analyzing the collection of sequencing reads to determine the number of clusters of sequencing reads includes: determining, by the one or more computing devices, a measure of similarity between a first nucleotide sequence of one or more first sequencing reads included the collection of sequencing reads and a second nucleotide sequence of one or more second sequencing reads included in the collection of sequencing reads; determining, by the one or more computing devices, that the measure of similarity is at least a threshold measure of similarity; and determining that the first nucleotide sequences and the second nucleotide sequences correspond to a same consensus sequence.

Aspect 22. The method of any one of aspects 14-21, wherein nucleotides of the individual nucleic acid representations are ordered such that a probability of the at least two nucleotides interacting to form a hairpin structure in nucleic acids corresponding to the individual nucleic acid representations is less than a threshold probability.

Aspect 23. The method of any one of aspects 14-22, wherein generating nucleic acid representations based on the string of characters includes: generating, by the one or more computing devices and for individual nucleic acid representations, a first segment that corresponds to an identifier of the individual nucleic acid representation and a second segment that corresponds to a portion of the digital data; and performing, by the one or more computing devices and for the individual nucleic acid representations, one or more encryption processes with respect to the second segment of the individual nucleic acid representations based on the first segment of the individual nucleic acid representations to generate a plurality of encoded nucleic acid representations.

Aspect 24. The method of aspect 23, wherein the one or more encryption processes include an XOR randomization process Aspect 25. The method of any one of aspects 14-24, wherein the second encoding scheme is linear and the string of characters is distributed among the nucleic acid representations according to a transverse arrangement such that a first portion of the string of characters is distributed at a first position of each of the nucleic acid representations and a second portion of the string of characters is distributed at a second position of each of the nucleic acid representations.

Aspect 26. The method of any one of aspects of claim 14-25, wherein the second encoding scheme is non-linear and the portion of the string of characters is distributed across positions of the individual nucleic acid representations such that a first character of the string of characters is represented at a first position of a first nucleic acid representation and is offset by one or more positions with respect to a second character of the string of characters that is represented at a second position of a second nucleic acid representation, wherein the first character and the second character are consecutive characters in the string of characters and the first nucleic acid representation and the second nucleic acid representation are ordered consecutively.

Aspect 27. A method comprising: obtaining, by one or more computing devices including one or more processors and memory, an amount of digital data; determining, by the one or more computing devices, a string of characters that corresponds to the digital data according to a first encoding scheme such that individual characters of the string of characters are represented by a nucleotide included in at least one of deoxyribonucleic acid (DNA) or ribonucleic acid (RNA); and generating, by the one or more computing devices, a plurality of nucleic acid representations based on the string of characters, wherein individual nucleic acid representations of the plurality of nucleic acid representations include a plurality of positions and a portion of the string of characters is distributed among the plurality of nucleic acid representations at an individual position across the plurality of nucleic acid representations according to a second encoding scheme.

Aspect 28. The method of aspect 27, wherein a number of the nucleic acid representations encoding the digital data is at least 500.

Aspect 29. The method of aspect 27 or 28, comprising: synthesizing oligonucleotides that correspond to the oligonucleotide representations; storing the oligonucleotides in a storage container; performing one or more sequencing operations to produce an amplification product that includes a plurality of oligonucleotides that correspond to individual oligonucleotide representations; and generating sequencing data that includes a plurality of sequencing reads, the plurality of sequencing reads corresponding to the plurality of oligonucleotides included in the amplification product.

Aspect 30. The method of aspect 29, comprising: analyzing, by the one or more computing devices, the plurality of sequencing reads to determine one or more sequencing reads of the plurality of sequencing reads that correspond to a nucleic acid representation of the plurality of nucleic acid representations; for a given position of the one or more sequencing reads, determining, by the one or more computing devices, an additional string of characters that corresponds to a nucleotide present at the given position of the one or more sequencing reads; and generating, by the one or more computing devices and using a decoding scheme, a requested portion of the digital data based on the additional string of characters.

Aspect 31. A system comprising: one or more processors; and memory storing computer-readable instructions that, when executed by the one or more processors, cause the one or more processors to perform operations comprising: obtaining an amount of digital data; determining a string of characters that corresponds to the digital data according to a first encoding scheme such that individual characters of the string of characters are represented by a nucleotide included in at least one of deoxyribonucleic acid (DNA) or ribonucleic acid (RNA); and generating a plurality of nucleic acid representations based on the string of characters, wherein individual nucleic acid representations of the plurality of nucleic acid representations include a plurality of positions and a portion of the string of characters is distributed among the plurality of nucleic acid representations at an individual position across the plurality of nucleic acid representations according to a second encoding scheme.

Aspect 32. The system of aspect 31, wherein a number of the nucleic acid representations encoding the digital data is at least 500.

Aspect 33. The system of aspect 31 or 32, wherein the memory stores additional computer-readable instructions that, when executed by the one or more processors, cause the one or more processors to perform additional operations comprising: accessing sequencing data that includes a plurality of sequencing reads, the plurality of sequencing reads corresponding to a plurality of oligonucleotides included in an amplification product that is producing by one or more sequencing operations, wherein the plurality of oligonucleotides correspond to individual oligonucleotide representations.

Aspect 34. The system of aspect 33, wherein the memory stores additional computer-readable instructions that, when executed by the one or more processors, cause the one or more processors to perform additional operations comprising: analyzing the plurality of sequencing reads to determine one or more sequencing reads of the plurality of sequencing reads that correspond to a nucleic acid representation of the plurality of nucleic acid representations; for a given position of the one or more sequencing reads, determining an additional string of characters that corresponds to a nucleotide present at the given position of the one or more sequencing reads; and generating, using a decoding scheme, a requested portion of the digital data based on the additional string of characters.

Aspect 35. A method comprising: receiving, by the one or more computing devices, a request to access at least a portion of the digital data; obtaining, by the one or more computing devices, a plurality of sequencing reads that correspond to nucleic acids synthesized according to the nucleic acid representations, wherein the plurality of sequencing reads indicate nucleotides present at individual positions of the nucleic acids; performing, by the one or more computing devices, a process to align individual positions of the plurality of sequencing reads to generate aligned sequencing reads; for a given position of the aligned sequencing reads, determining, by the one or more computing devices, an additional string of characters that corresponds to a nucleotide present at the given position of the aligned sequencing reads; and generating, by the one or more computing devices and using a decoding scheme, a requested portion of the digital data based on the additional string of characters.

Aspect 36. The method of aspect 35, wherein a number of nucleotides included in the nucleic acids corresponding to the nucleic acid representations is from about 100 nucleotides to about 8000 nucleotides.

Aspect 37. The method of aspect 35 or 36, comprising: causing, by the one or more computing devices, the requested portion of the digital data to be accessible to at least one computing device such that the at least one computing device can cause the requested portion of the digital data to at least one of be stored in memory related to the at least one computing device, be displayed by a display device related to the at least one computing device, or be used in one or more operations performed by an application executed by the at least one computing device.

Aspect 38. A system comprising: one or more processors; and memory storing computer-readable instructions that, when executed by the one or more processors, cause the one or more processors to perform operations comprising: receiving a request to access at least a portion of the digital data; obtaining a plurality of sequencing reads that correspond to nucleic acids synthesized according to the nucleic acid representations, wherein the plurality of sequencing reads indicate nucleotides present at individual positions of the nucleic acids; performing a process to align individual positions of the plurality of sequencing reads to generate aligned sequencing reads; for a given position of the aligned sequencing reads, determining an additional string of characters that corresponds to a nucleotide present at the given position of the aligned sequencing reads; and generating, using a decoding scheme, a requested portion of the digital data based on the additional string of characters.

Aspect 39. The system of aspect 38, wherein a number of nucleotides included in the nucleic acids corresponding to the nucleic acid representations is from about 100 nucleotides to about 8000 nucleotides.

Aspect 40. The system of aspect 38 or 39, wherein the memory stores additional computer-readable instructions that, when executed by the one or more processors, cause the one or more processors to perform additional operations comprising: causing the requested portion of the digital data to be accessible to at least one computing device such that the at least one computing device can cause the requested portion of the digital data to at least one of be stored in memory related to the at least one computing device, be displayed by a display device related to the at least one computing device, or be used in one or more operations performed by an application executed by the at least one computing device.

Aspect 41. A method comprising: obtaining, by one or more computing devices including one or more processors and memory, an amount of digital data; determining, by the one or more computing devices, a string of characters that corresponds to the digital data according to an encoding scheme such that individual characters of the string of characters are represented by a nucleotide included in at least one of deoxyribonucleic acid (DNA) or ribonucleic acid (RNA); generating, by the one or more computing devices, nucleic acid representations based on the string of characters, wherein individual nucleic acid representations include a first segment that corresponds to an identifier of the individual nucleic acid representation and a second segment that corresponds to a portion of the digital data; and performing, by the one or more computing devices and for the individual nucleic acid representations, one or more encryption processes with respect to the second segment of the individual nucleic acid representations based on the first segment of the individual nucleic acid representations to generate a plurality of encoded nucleic acid representations.

Aspect 42. The method of aspect 41, wherein the first segment is an encryption key and the one or more encryption processes include an XOR randomization process.

Aspect 43. The method of aspect 41 or 42, comprising: receiving, by the one or more computing devices, a request to access at least a portion of the digital data; obtaining, by the one or more computing devices, a plurality of sequencing reads that correspond to nucleic acids synthesized according to the nucleic acid representations, wherein the plurality of sequencing reads indicate nucleotides present at individual positions of the nucleic acids; determining, by the one or more computing devices and for individual sequencing reads of the plurality of sequencing reads, a first portion of the individual sequences reads that correspond to the first segment and a second portion of the individual sequencing reads that corresponds to a payload of encrypted data; and performing, by the one or more computing devices and for the individual sequencing reads, one or more decoding processes to decode the payload of the encrypted data using the first segment to generate decoded sequencing reads that include the second segment of the individual nucleic acid representations that correspond to the individual sequencing reads.

Aspect 44. The method of aspect 43, wherein: the nucleic acid representations are generated such that a portion of the string of characters is distributed among the nucleic acid representations at an individual position across the nucleic acid representations; and the method comprises: performing, by the one or more computing devices, a process to align individual positions of the decoded sequencing reads to generate aligned sequencing reads; for a given position of the nucleic acids corresponding to the aligned sequencing reads, determining, by the one or more computing devices, an additional string of characters that corresponds to a nucleotide present at the given position of the aligned sequencing reads; and generating, by the one or more computing devices and using a decoding scheme, a requested portion of the digital data based on the additional string of characters.

Aspect 45. A system comprising: one or more processors; and memory storing computer-readable instructions that, when executed by the one or more processors, cause the one or more processors to perform operations comprising: obtaining an amount of digital data; determining a string of characters that corresponds to the digital data according to an encoding scheme such that individual characters of the string of characters are represented by a nucleotide included in at least one of deoxyribonucleic acid (DNA) or ribonucleic acid (RNA); generating nucleic acid representations based on the string of characters, wherein individual nucleic acid representations include a first segment that corresponds to an identifier of the individual nucleic acid representation and a second segment that corresponds to a portion of the digital data; and performing, for the individual nucleic acid representations, one or more encryption processes with respect to the second segment of the individual nucleic acid representations based on the first segment of the individual nucleic acid representations to generate a plurality of encoded nucleic acid representations.

Aspect 46. The system of aspect 45, wherein the first segment is an encryption key and the one or more encryption processes include an XOR randomization process.

Aspect 47. The system of aspect 45 or 46, wherein the memory stores additional computer-readable instructions that, when executed by the one or more processors, cause the one or more processors to perform additional operations comprising: receiving a request to access at least a portion of the digital data; obtaining a plurality of sequencing reads that correspond to nucleic acids synthesized according to the nucleic acid representations, wherein the plurality of sequencing reads indicate nucleotides present at individual positions of the nucleic acids; determining, for individual sequencing reads of the plurality of sequencing reads, a first portion of the individual sequences reads that correspond to the first segment and a second portion of the individual sequencing reads that corresponds to a payload of encrypted data; and performing, for the individual sequencing reads, one or more decoding processes to decode the payload of the encrypted data using the first segment to generate decoded sequencing reads that include the second segment of the individual nucleic acid representations that correspond to the individual sequencing reads.

Aspect 48. The system of aspect 47, wherein: the nucleic acid representations are generated such that a portion of the string of characters is distributed among the nucleic acid representations at an individual position across the nucleic acid representations; and the memory stores additional computer-readable instructions that, when executed by the one or more processors, cause the one or more processors to perform additional operations comprising: performing a process to align individual positions of the decoded sequencing reads to generate aligned sequencing reads; for a given position of the nucleic acids corresponding to the aligned sequencing reads, determining an additional string of characters that corresponds to a nucleotide present at the given position of the aligned sequencing reads; and generating, using a decoding scheme, a requested portion of the digital data based on the additional string of characters.

What is claimed is:

1. A system comprising:
one or more processors; and
memory storing computer-readable instructions that, when executed by the one or more processors, cause the one or more processors to perform operations comprising:
obtaining an amount of digital data stored in one or more data files;
determining a string of characters that corresponds to the digital data according to a first encoding scheme such that individual characters of the string of characters are represented by a nucleotide included in at least one of deoxyribonucleic acid (DNA) or ribonucleic acid (RNA);
generating nucleic acid representations based on the string of characters, wherein individual nucleic acid representations include a plurality of positions and a portion of the string of characters is distributed among the nucleic acid representations at an individual position across the nucleic acid representations according to a second encoding scheme;
receiving a request to access at least a portion of the digital data;
obtaining a plurality of sequencing reads that correspond to nucleic acids synthesized according to the nucleic acid representations, wherein the plurality of sequencing reads indicate nucleotides present at individual positions of the nucleic acids;

performing a process to align individual positions of the plurality of sequencing reads to generate aligned sequencing reads;

for a given position of the aligned sequencing reads, determining an additional string of characters that corresponds to a nucleotide present at the given position of the aligned sequencing reads; and generating, using a decoding scheme, a requested portion of the digital data based on the additional string of characters.

2. The system of claim 1, wherein the nucleic acid representations comprise segments having no greater than a threshold frequency of a given pattern of one or more nucleotides.

3. The system of claim 2, wherein the given pattern is repetition of a pair of nucleotides at a threshold number of consecutive pairs of positions of the nucleic acid representations.

4. The system of claim 2, wherein the given pattern is repetition of a set of three nucleotides at a threshold number of consecutive positions of the nucleic acid representations.

5. The system of claim 1, wherein individual sequencing reads of the plurality of sequences reads include:
a first segment indicating a primer used in a sequencing process that generates the plurality of sequencing reads;
a second segment indicating a location of the individual sequencing read with respect to an order in which the plurality of sequencing reads are to be aligned; and
a third segment indicating a payload that corresponds to a number of nucleotides that encode a portion of the digital data.

6. The system of claim 1, wherein the memory stores additional computer-readable instructions that, when executed by the one or more processors, cause the one or more processors to perform additional operations comprising:
for a first position of the aligned sequencing reads, determining a nucleotide present at the first position of each of the aligned sequencing reads to generate a first portion of the additional string of characters; and
for a second position of the aligned sequencing reads, determining an additional nucleotide present at the second position of each of the aligned sequencing reads to generate a second portion of the additional string of characters.

7. The system of claim 1, wherein the memory stores additional computer-readable instructions that, when executed by the one or more processors, cause the one or more processors to perform additional operations comprising:
obtaining a collection of sequencing reads that correspond to nucleic acids synthesized according to the nucleic acid representations;
analyzing the collection of sequencing reads to determine a number of clusters of sequencing reads, wherein individual clusters of the number of sequencing reads correspond to one or more copies of a given nucleic acid that was subject to one or more sequencing operations; and
determining a plurality of consensus sequencing reads that individually correspond to an individual cluster of sequencing reads;
wherein the plurality of sequencing reads includes the plurality of consensus sequencing reads.

8. The system of claim 7, wherein the memory stores additional computer-readable instructions that, when executed by the one or more processors, cause the one or more processors to analyze the collection of sequencing reads to determine the number of clusters of sequencing reads by:
determining a measure of similarity between a first nucleotide sequence of one or more first sequencing reads included the collection of sequencing reads and a second nucleotide sequence of one or more second sequencing reads included in the collection of sequencing reads;
determining that the measure of similarity is at least a threshold measure of similarity; and
determining that the first nucleotide sequences and the second nucleotide sequences correspond to a same consensus sequence.

9. The system of claim 1, wherein nucleotides of the individual nucleic acid representations are ordered such that a probability of the at least two nucleotides interacting to form a hairpin structure in nucleic acids corresponding to the individual nucleic acid representations is less than a threshold probability.

10. The system of claim 1, wherein the memory stores additional computer-readable instructions that, when executed by the one or more processors, cause the one or more processors to generate nucleic acid representations based on the string of characters by:
generating, for individual nucleic acid representations, a first segment that corresponds to an identifier of the individual nucleic acid representation and a second segment that corresponds to a portion of the digital data; and
performing, for the individual nucleic acid representations, one or more encryption processes with respect to the second segment of the individual nucleic acid representations based on the first segment of the individual nucleic acid representations to generate a plurality of encoded nucleic acid representations.

11. The system of claim 10, wherein the one or more encryption processes include an XOR randomization process.

12. The system of claim 1, wherein the second encoding scheme is linear and the string of characters is distributed among the nucleic acid representations according to a transverse arrangement such that a first portion of the string of characters is distributed at a first position of each of the nucleic acid representations and a second portion of the string of characters is distributed at a second position of each of the nucleic acid representations.

13. The system of claim 1, wherein the second encoding scheme is non-linear and the portion of the string of characters is distributed across positions of the individual nucleic acid representations such that a first character of the string of characters is represented at a first position of a first nucleic acid representation and is offset by one or more positions with respect to a second character of the string of characters that is represented at a second position of a second nucleic acid representation, wherein the first character and the second character are consecutive characters in the string of characters and the first nucleic acid representation and the second nucleic acid representation are ordered consecutively.

14. A method comprising:
obtaining, by one or more computing devices including one or more processors and memory, an amount of digital data;
determining, by the one or more computing devices, a string of characters that corresponds to the digital data according to an encoding scheme such that individual characters of the string of characters are represented by a nucleotide included in at least one of deoxyribonucleic acid (DNA) or ribonucleic acid (RNA); and generating, by the one or more computing devices, a plurality of nucleic acid representations based on the string of characters, wherein individual nucleic acid representations of the plurality of nucleic acid representations include a plurality of positions and a portion of the string of characters is distributed among the plurality of nucleic acid representations at an individual position across the plurality of nucleic acid representations according to a pattern.

15. The method of claim 14, wherein a number of the nucleic acid representations encoding the digital data is at least 500.

16. The method of claim 14, comprising:

synthesizing oligonucleotides that correspond to the oligonucleotide representations;

storing the oligonucleotides in a storage container;

performing one or more sequencing operations to produce an amplification product that includes a plurality of oligonucleotides that correspond to individual oligonucleotide representations; and generating sequencing data that includes a plurality of sequencing reads, the plurality of sequencing reads corresponding to the plurality of oligonucleotides included in the amplification product.

17. The method of claim 16, comprising:

analyzing, by the one or more computing devices, the plurality of sequencing reads to determine one or more sequencing reads of the plurality of sequencing reads that correspond to a nucleic acid representation of the plurality of nucleic acid representations;

for a given position of the one or more sequencing reads, determining, by the one or more computing devices, an additional string of characters that corresponds to a nucleotide present at the given position of the one or more sequencing reads; and generating, by the one or more computing devices and using a decoding scheme, a requested portion of the digital data based on the additional string of characters.

18. A method comprising:

receiving, by the one or more computing devices, a request to access at least a portion of the digital data;

obtaining, by the one or more computing devices, a plurality of sequencing reads that correspond to nucleic acids synthesized according to the nucleic acid representations, wherein the plurality of sequencing reads indicate nucleotides present at individual positions of the nucleic acids;

performing, by the one or more computing devices, a process to align individual positions of the plurality of sequencing reads to generate aligned sequencing reads;

for a given position of the aligned sequencing reads, determining, by the one or more computing devices, an additional string of characters that corresponds to a nucleotide present at the given position of the aligned sequencing reads; and generating, by the one or more computing devices and using a decoding scheme, a requested portion of the digital data based on the additional string of characters.

19. The method of claim 18, wherein a number of nucleotides included in the nucleic acids corresponding to the nucleic acid representations is from about 100 nucleotides to about 8000 nucleotides.

20. The method of claim 18, comprising:

causing, by the one or more computing devices, the requested portion of the digital data to be accessible to at least one computing device such that the at least one computing device can cause the requested portion of the digital data to at least one of be stored in memory related to the at least one computing device, be displayed by a display device related to the at least one computing device, or be used in one or more operations performed by an application executed by the at least one computing device.

* * * * *